(12) United States Patent
Herscher et al.

(10) Patent No.: US 11,071,583 B2
(45) Date of Patent: Jul. 27, 2021

(54) POWER GENERATING AND CONTROL APPARATUS FOR THE TREATMENT OF TISSUE

(71) Applicant: Vessix Vascular, INc., Laguna Hills, CA (US)

(72) Inventors: Bret Herscher, Cupertino, CA (US); David Krawzsenek, El Cajon, CA (US); Aaron LeBarge, San Diego, CA (US); Joseluis Espinosa, San Diego, CA (US); Michael Perry, Los Altos, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 619 days.

(21) Appl. No.: 15/008,103

(22) Filed: Jan. 27, 2016

(65) Prior Publication Data
US 2016/0135883 A1 May 19, 2016

Related U.S. Application Data

(63) Continuation of application No. 13/066,347, filed on Apr. 11, 2011, now Pat. No. 9,277,955.
(Continued)

(51) Int. Cl.
*A61B 18/12* (2006.01)
*A61B 18/14* (2006.01)
(Continued)

(52) U.S. Cl.
CPC ...... *A61B 18/1492* (2013.01); *A61B 18/1206* (2013.01); *A61B 17/22012* (2013.01);
(Continued)

(58) Field of Classification Search
CPC .......... A61B 17/22012; A61B 18/1206; A61B 18/1492; A61B 18/245;
(Continued)

(56) References Cited

U.S. PATENT DOCUMENTS 5,423,882 A * 6/1995 Jackman ............ A61B 18/1492
607/122
5,728,139 A 3/1998 Post
(Continued)

FOREIGN PATENT DOCUMENTS

JP 07799991 3/1995
JP 2000116140 4/2000

*Primary Examiner* — Daniel W Fowler
(74) *Attorney, Agent, or Firm* — Kacvinsky Daisak Bluni PLLC

(57) ABSTRACT

Apparatus, systems, and methods are provided for the generation and control of energy delivery in a dosage to elicit a therapeutic response in diseased tissue. A balloon catheter can have electrodes attached to a power generator and controller such that the balloon and electrodes contact tissue during energy treatment. Energy selectively may be applied to tissue based on measured impedance to achieve gentle heating. Calibration of the apparatus and identification of attached accessories by computing the circuit impedance prior to energy dosage facilitate regulation of power delivery about a set point. Energy delivery can be controlled to achieve substantially uniform bulk tissue temperature distribution. Energy delivery may beneficially affect nerve activity.

20 Claims, 9 Drawing Sheets

Related U.S. Application Data

(60) Provisional application No. 61/342,191, filed on Apr. 9, 2010.

(51) Int. Cl.
  *A61B 17/22* (2006.01)
  *A61B 18/24* (2006.01)
  *A61B 18/00* (2006.01)
  *A61B 18/18* (2006.01)
  *A61N 7/02* (2006.01)

(52) U.S. Cl.
  CPC ..... *A61B 18/245* (2013.01); *A61B 2018/0022* (2013.01); *A61B 2018/00214* (2013.01); *A61B 2018/00422* (2013.01); *A61B 2018/00434* (2013.01); *A61B 2018/00577* (2013.01); *A61B 2018/00642* (2013.01); *A61B 2018/00684* (2013.01); *A61B 2018/00702* (2013.01); *A61B 2018/00875* (2013.01); *A61B 2018/00898* (2013.01); *A61B 2018/1861* (2013.01); *A61N 7/022* (2013.01)

(58) Field of Classification Search
  CPC .. A61B 2018/00214; A61B 2018/0022; A61B 2018/00422; A61B 2018/00434; A61B 2018/00577; A61B 2018/00642; A61B 2018/00684; A61B 2018/00702; A61B 2018/00875; A61B 2018/00898; A61B 2018/1861
  See application file for complete search history.

(56) References Cited

U.S. PATENT DOCUMENTS

| | | | |
|---|---|---|---|
| 5,831,477 A | 11/1998 | Tsumura | |
| 5,836,943 A | 11/1998 | Miller, III | |
| 5,891,134 A * | 4/1999 | Goble | A61B 18/08 606/191 |
| 5,971,980 A * | 10/1999 | Sherman | A61B 17/22012 606/34 |
| 6,053,909 A * | 4/2000 | Shadduck | A61B 18/148 606/3 |
| 6,083,223 A * | 7/2000 | Baker | A61B 18/1445 606/49 |
| 6,258,087 B1 * | 7/2001 | Edwards | A61B 18/12 600/374 |
| 2002/0115997 A1 * | 8/2002 | Truckai | A61B 18/1445 606/51 |
| 2004/0187875 A1 * | 9/2004 | He | A61B 18/1492 128/898 |
| 2005/0171523 A1 | 8/2005 | Rubinsky et al. | |
| 2005/0203505 A1 * | 9/2005 | Megerman | A61B 18/02 606/41 |
| 2006/0064084 A1 * | 3/2006 | Haemmerich | A61B 18/1477 606/41 |
| 2006/0079882 A1 * | 4/2006 | Swoyer | A61B 18/1492 606/41 |
| 2007/0019109 A1 | 1/2007 | Lombardi et al. | |
| 2008/0114350 A1 * | 5/2008 | Park | A61B 18/1206 606/34 |
| 2008/0183251 A1 * | 7/2008 | Azar | A61B 18/14 607/101 |
| 2008/0234574 A1 | 9/2008 | Hancock et al. | |
| 2008/0255642 A1 * | 10/2008 | Zarins | A61B 18/1206 607/99 |
| 2010/0030210 A1 | 2/2010 | Paulus | |

\* cited by examiner

POWER GENERATING AND CONTROL APPARATUS FOR THE TREATMENT OF TISSUE

CROSS-REFERENCES TO RELATED APPLICATIONS

This application is a Continuation of U.S. application Ser. No. 13/066,347 filed Apr. 11, 2011 which claims the benefit under 35 USC 119(e) of U.S. Provisional Application No. 61/342,191 filed Apr. 9, 2010; the full disclosure of which is incorporated herein by reference in its entirety for all purposes.

The subject matter of this application is related to that of U.S. patent application Ser. No. 11/392,231, filed on Mar. 28, 2006, entitled "Tuned RF Energy for Selective Treatment of Atheroma and Other Target Tissues and/or Structures"; U.S. patent application Ser. No. 10/938,138, filed on Sep. 10, 2004, entitled "Selectable Eccentric Remodeling and/or Ablation of Atherosclerotic Material"; U.S. Provisional Application No. 60/852,787, filed on Oct. 18, 2006, entitled "Tuned RF Energy and Electrical Tissue Characterization For Selective Treatment Of Target Tissues"; U.S. Provisional Application No. 60/921,973, filed on Apr. 4, 2007, entitled "Tuned RF Energy and Electrical Tissue Characterization For Selective Treatment Of Target Tissues"; U.S. patent application Ser. No. 11/975,651, filed on Oct. 18, 2007, entitled "Tuned RF Energy and Electrical Tissue Characterization For Selective Treatment Of Target Tissues"; U.S. patent application Ser. No. 12/617,519, filed on Nov. 12, 2009, entitled "Selective Accumulation of Energy With or Without Knowledge of Tissue Topography"; U.S. patent application Ser. No. 11/975,474, filed on Oct. 18, 2007, entitled "Inducing Desirable Temperature Effects on Body Tissue"; U.S. patent application Ser. No. 11/975,383, filed on Oct. 18, 2007, entitled "System for Inducing Desirable Temperature Effects On Body Tissue"; U.S. patent application Ser. No. 12/616,720, filed on Nov. 13, 2009, entitled "Selective Drug Delivery in a Lumen"; U.S. application Ser. No. 12/564,268, filed on Sep. 22, 2009, entitled "Inducing Desirable Temperature Effects on Body Tissue Using Alternate Energy Sources"; and U.S. Provisional Application 61/177,744, filed on May 13, 2009, entitled "Directional Delivery of Energy and Bioactives", the full disclosures of which are incorporated herein by reference.

BACKGROUND OF THE INVENTION

Field of the Invention

The present invention is generally related to medical devices, systems, and methods which apply (or otherwise make use of) energy, as well as to other fields in which accurate control over electrical energy is beneficial. In exemplary embodiments, the invention provides an energy generating and control apparatus for the selective delivery of energy dosage during catheter-based treatment for luminal diseases, particularly for atherosclerotic plaque, vulnerable or "hot" plaque, and the like.

Discussion of Related Art

Physicians use catheters to gain access to, and repair, interior tissues of the body, particularly within the lumens of the body such as blood vessels. For example, balloon angioplasty and other catheters often are used to open arteries that have been narrowed due to atherosclerotic disease.

Balloon angioplasty is often effective at opening an occluded blood vessel, but the trauma associated with balloon dilation can impose significant injury, so that the benefits of balloon dilation may be limited in time. Stents are commonly used to extend the beneficial opening of the blood vessel.

Stenting, in conjunction with balloon dilation, is often the preferred treatment for atherosclerosis. In stenting, a collapsed metal framework is mounted on a balloon catheter that is introduced into the body. The stent is manipulated into the site of occlusion and expanded in place by the dilation of the underlying balloon. Stenting has gained widespread acceptance, and produces generally acceptable results in many cases. Along with treatment of blood vessels, particularly the coronary arteries, stents can also be used in treating many other tubular obstructions within the body, such as for treatment of reproductive, gastrointestinal, and pulmonary obstructions.

Restenosis or a subsequent narrowing of the body lumen after stenting has occurred in a significant number of cases. More recently, drug coated stents (such as Johnson and Johnson's Cypher™ stent, the associated drug comprising Sirolimus™) have demonstrated a markedly reduced restenosis rate, and others are developing and commercializing alternative drug eluting stents. In addition, work has also been initiated with systemic drug delivery (intravenous or oral) that may also improve the procedural angioplasty success rates.

While drug-eluting stents appear to offer significant promise for treatment of atherosclerosis in many patients, there remain many cases where stents either cannot be used or present significant disadvantages. Generally, stenting leaves an implant in the body. Such implants can present risks, including mechanical fatigue, corrosion, and the like, particularly when removal of the implant is difficult and involves invasive surgery. Stenting may have additional disadvantages for treating diffuse artery disease, for treating bifurcations, for treating areas of the body susceptible to crush, and for treating arteries subject to torsion, elongation, and shortening.

A variety of modified restenosis treatments or restenosis-inhibiting occlusion treatment modalities have also been proposed, including intravascular radiation, cryogenic treatments, ultrasound energy, and the like, often in combination with balloon angioplasty and/or stenting. While these and different approaches show varying degrees of promise for decreasing the subsequent degradation in blood flow following angioplasty and stenting, the trauma initially imposed on the tissues by angioplasty remains problematic.

More recently, still further disadvantages of dilation have come to light. These include the existence of vulnerable plaque, which can rupture and release materials that may cause myocardial infarction or heart attack.

A number of alternatives to stenting and balloon angioplasty so as to open stenosed arteries have also been proposed. For example, a wide variety of atherectomy devices and techniques have been disclosed and attempted. Despite the disadvantages and limitations of angioplasty and stenting, atherectomy has not gained the widespread use and success rates of dilation-based approaches.

Additionally, methods in the art of debulking diseased tissue to reduce or eliminate lesions, such as atherectomy and ablation, generally provide few if any means for protecting healthy tissue from being damaged through the course of treating diseased tissue.

In light of the above, it would be advantageous to provide new devices, systems, and methods for remodeling of the lumens of the body, and particularly tissue of the blood vessels. It would further be desirable to avoid significant cost or complexity while providing structures which could remodel body lumens without having to resort to the trauma of extreme dilation, damage to neighboring healthy tissue, and to allow the opening of blood vessels and other body lumens which are not suitable for stenting.

BRIEF SUMMARY OF THE INVENTION

The present invention relates to the treatment of tissue through the delivery of energy in a controlled dosage. Tissue may be targeted by applying energy, making tissue characterization analysis, and further selectively energizing a plurality of energy delivery surfaces through the use of an energy source with a controller.

In exemplary embodiments, the apparatus for power delivery may comprise a power generating circuit further comprising: a power generating source, an amplifier block, a power output set point controller, voltage and current feedback at the point of power delivery used to measure impedance at the power delivery target, a peak effective power sensor block receiving the voltage and current feedback, and a Proportional, Integral, Derivative (PID) controller receiving a signals from the power output set point controller and the peak effective power sensor block, whereby the PID controller modulates total input voltage to the power amplifier block such that the output of power from the circuit is maintained within a range about the power output set point in response to measured impedance at the power delivery target.

In some exemplary embodiments output power is Radio Frequency (RF) power while in alternate exemplary embodiments power may be in the form of ultrasound, microwave, laser, or other suitable forms of energy.

In some exemplary embodiments the apparatus for delivery may be further comprised of a catheter, wherein the catheter may be further comprised to have a plurality of energy delivery surfaces, most preferably a plurality of energy delivery surfaces mounted to an inflatable balloon.

In some exemplary embodiments there is provided a method for preferably calibrating the apparatus comprised of using a variety of loads to calculate power circuit impedance with vector network analysis such that the measure of real-time change in circuit load impedance during power generation may represent the real-time change in impedance at the power delivery target of the apparatus.

In some exemplary embodiments there is provided a method comprising identifying an accessory attached to the apparatus by repeating calibration to ascertain the type of attached accessory based on its impedance characteristics.

In some exemplary embodiments there is provided a method of applying energy in a controlled manner to achieve a substantially uniform bulk temperature distribution in target tissue.

In some exemplary embodiments there is provided a method for applying energy to nerve tissue to alter the activity of the nerve for the purpose of achieving a beneficial biological response.

Preferred embodiments of the present invention may be used in procedures for achieving therapeutic biologic effects in tissue. Most preferably, the present invention may be used at any point and time before, during, and/or after an angioplasty procedure.

In another aspect, the invention provides a power generating apparatus for treatment of a target tissue. The power generating apparatus comprises a frequency synthesizer generating a frequency signal. A power amplifier operatively couples the frequency synthesizer to a power output. The output is coupleable to the target tissue, and a power sensor is configured to receive voltage and current feedback from the target tissue, and to output measured impedance at the target tissue. A controller couples the power sensor to the power amplifier. The controller has an input for receiving a power set point and transmits, in response to the power set point and the measured impedance at the target tissue, a modulating signal to the power amplifier such that power output from the power amplifier to the target tissue per the frequency signal is maintained within a desired range about the power set point.

Optionally, the frequency synthesizer comprises a digital frequency synthesizer such as a Direct Digital Synthesizer (DDS), and a digital-to-analog converter couples the frequency synthesizer to the power amplifier. The energy output from the apparatus to the target tissue typically comprises RF energy, but may alternatively comprise microwave energy or the like. In many embodiments, the power generating apparatus is included in a system, with the system also including an elongate catheter. The catheter may have an elongate flexible catheter body with a distal end configured for advancing into a blood vessel. A connector can be coupled to a proximal end of the body, with the connector being configured to couple to the output so that, in use, the catheter couples the output to the target tissue adjacent the distal end. The impedance of the target tissue as measured by the power generating apparatus of the system is often independent of an impedance of the power generating apparatus, the catheter body, and/or the like.

In another aspect, the invention provides a calibration module for calibrating an RF system in preparation for treatment of a target tissue. The RF system comprises a power generating apparatus including an impedance measurement circuit. The module comprises a first input for receiving a first impedance from the impedance measurement circuit of the power generating apparatus. The first impedance corresponding to a low circuit load on the power generating apparatus prior to coupling of the power generating apparatus to the target tissue. A second input similarly receives a second impedance from the impedance measurement circuit but corresponding to a high circuit load on the power generating apparatus (again prior to coupling of the power generating apparatus to the target tissue). A third input receives a similar third impedance from the impedance measurement circuit between the high load and the low load. A processor is configured to calculate system impedance using the measured impedances so as to facilitate, in response to a measure of real-time changes in overall circuit load impedance during power application to the target tissue, changes in impedance at the target tissue. The overall circuit load impedance comprising impedance of the power generating apparatus and the impedance at target tissue.

Typically, the RF system further comprises a catheter or other coupling device for coupling the power generating apparatus to the target tissue. More generally, the overall circuit of the systems described herein may, during use, include a power generating circuit, a power output target circuit, and a coupling circuit, with each of these portions of the overall system circuit contributing respective impedance portions to the overall impedance of the system. To help more accurately characterize the impedance contributions of these portions of the overall circuit, and to more accurately measure impedance at the target tissue (or other power output target), the processor can be configured to calculate another system impedance of the power generating apparatus and the catheter after coupling of the catheter to the power generating apparatus and before coupling of the catheter to the target tissue.

DETAILED DESCRIPTION OF THE INVENTION

Embodiments of the present invention relate to a power generating and control apparatus, often for the treatment of targeted tissue in order to achieve a therapeutic effect. Preferably, the target tissue is luminal tissue, which may further comprise diseased tissue such as that found in arterial disease.

While the disclosure focuses on the use of the technology in the vasculature, the technology would also be useful for other luminal obstructions. Other anatomical structures in which the present invention may be used are the esophagus, the oral cavity, the nasopharyngeal cavity, the auditory tube and tympanic cavity, the sinus of the brain, the arterial system, the venous system, the heart, the larynx, the trachea, the bronchus, the stomach, the duodenum, the ileum, the colon, the rectum, the bladder, the ureter, the ejaculatory duct, the vas deferens, the urethra, the uterine cavity, the vaginal canal, and the cervical canal.

Devices for heating tissue using RF, ultrasound, microwave and laser energies have been disclosed in U.S. patent application Ser. No. 11/975,474, filed on Oct. 18, 2007, entitled "Inducing Desirable Temperature Effects on Body Tissue", U.S. patent application Ser. No. 11/975,383, filed on Oct. 18, 2007, entitled "System for Inducing Desirable Temperature Effects On Body Tissue", U.S. patent application Ser. No. 11/122,263, filed on May 3, 2005, entitled "Imaging and Eccentric Atherosclerotic Material Laser Remodeling and/or Ablation Catheter" and U.S. application Ser. No. 12/564,268, filed on Sep. 22, 2009, entitled "Inducing Desirable Temperature Effects on Body Tissue Using Alternate Energy Sources", the full disclosures of which are incorporated herein by reference, may be combined with the present invention.

Power Generation and Control

In many embodiments of the present invention, the power generating and control apparatus may include internal circuitry 400, control software, a user interface 102, and power generation and control enclosure 101 housing the circuitry 400 and user interface 102.

Figure 1:
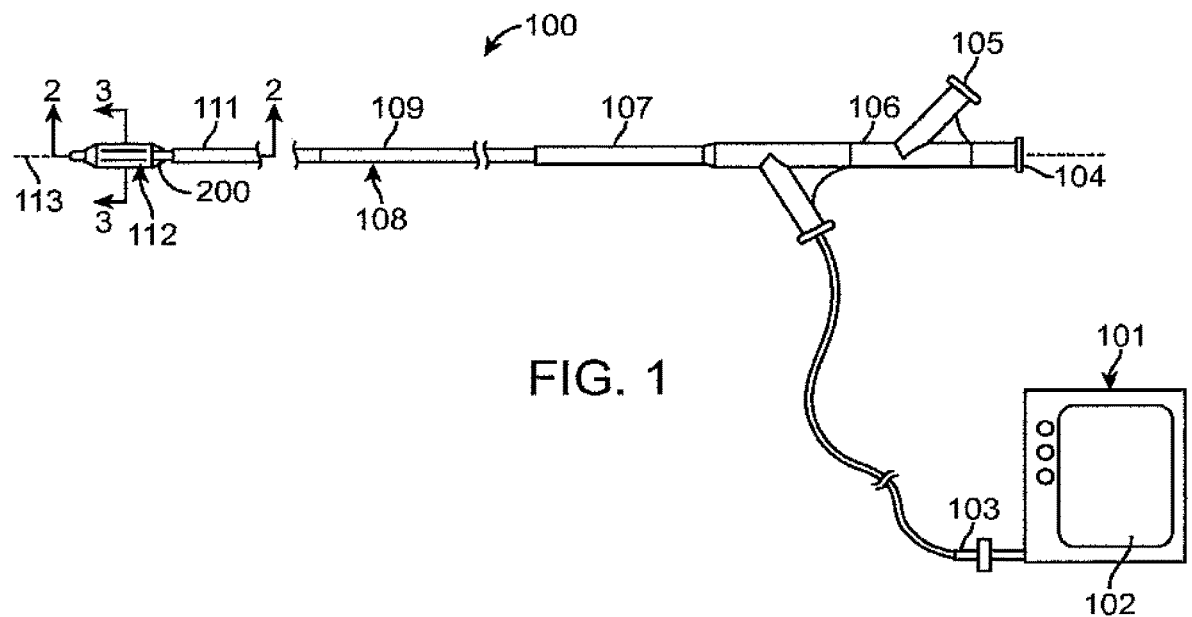
FIG. 1 schematically illustrates one embodiment of a power generation and control apparatus for use with a balloon catheter having electrodes in a power system.
Figure 4:
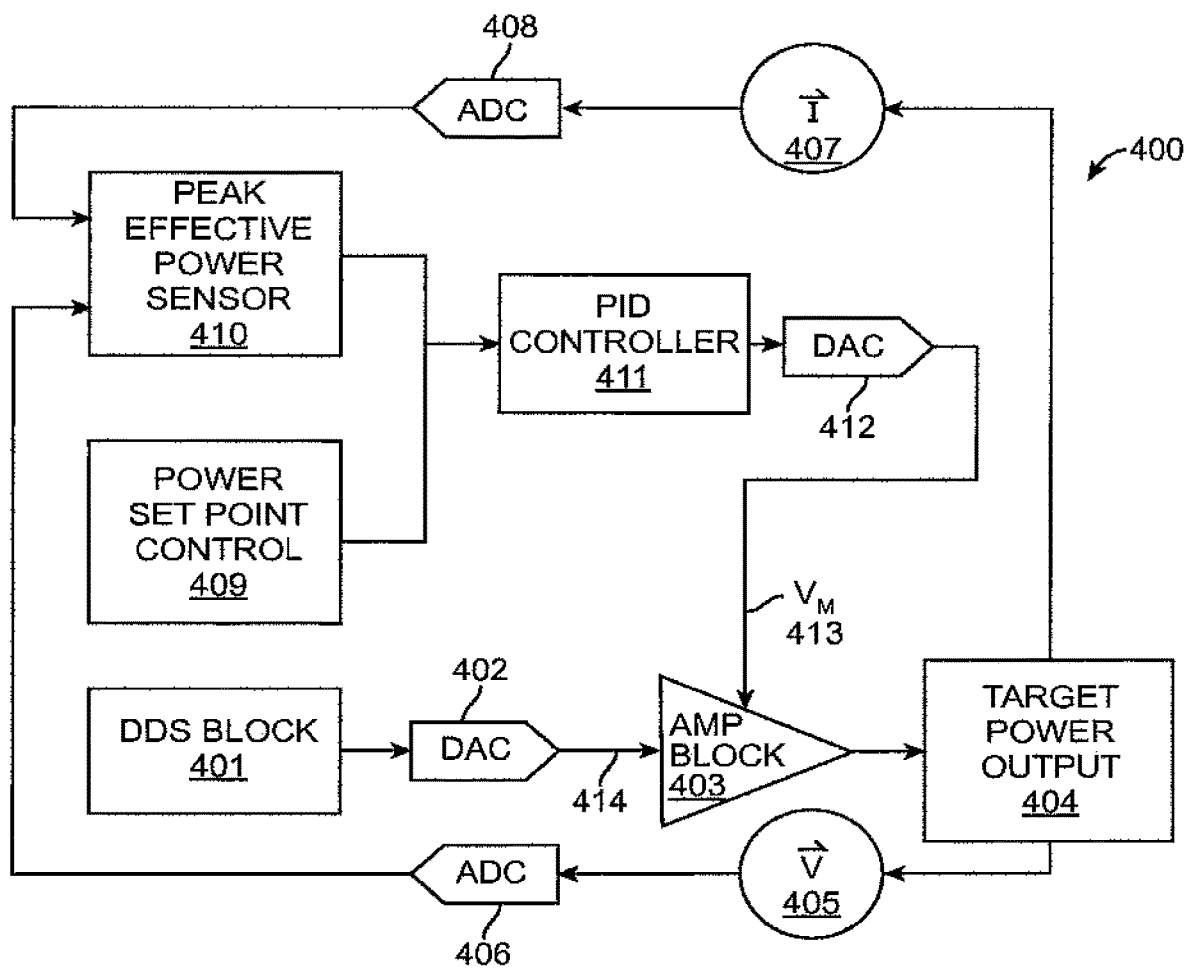
FIG. 4 schematically illustrates one embodiment of a power generation and control circuit.

Referring to FIGS. 1 and 4, the internal circuitry 400, housed within the enclosure 101, may include a direct digital synthesizer (DDS) block 401 whose digital code output may be preferably passed through digital-to-analog converter (DAC) 402. DAC 402 converts the digital code signal from DDS block 401 to an analog voltage signal 414. Voltage signal 414 and an analog modulating voltage signal 413 preferably pass through amplifier block 403, resulting in target power output 404. Measurements of voltage and current load at the target power output 404 may be measured by voltage sensor 405 and current sensor 407, preferably the signals from which may be passed through analog-to-digital converters (ADC) 406 and 408 respectively. The digital voltage signal from ADC 406 and the digital current signal from ADC 408 are preferably received by peak effective power sensor 410, where the effective power output of the power generation and control apparatus at the power delivery target 404 may be measured in real-time. Power set point control 409 is based on software-programmed operating parameters.

Figure 5:
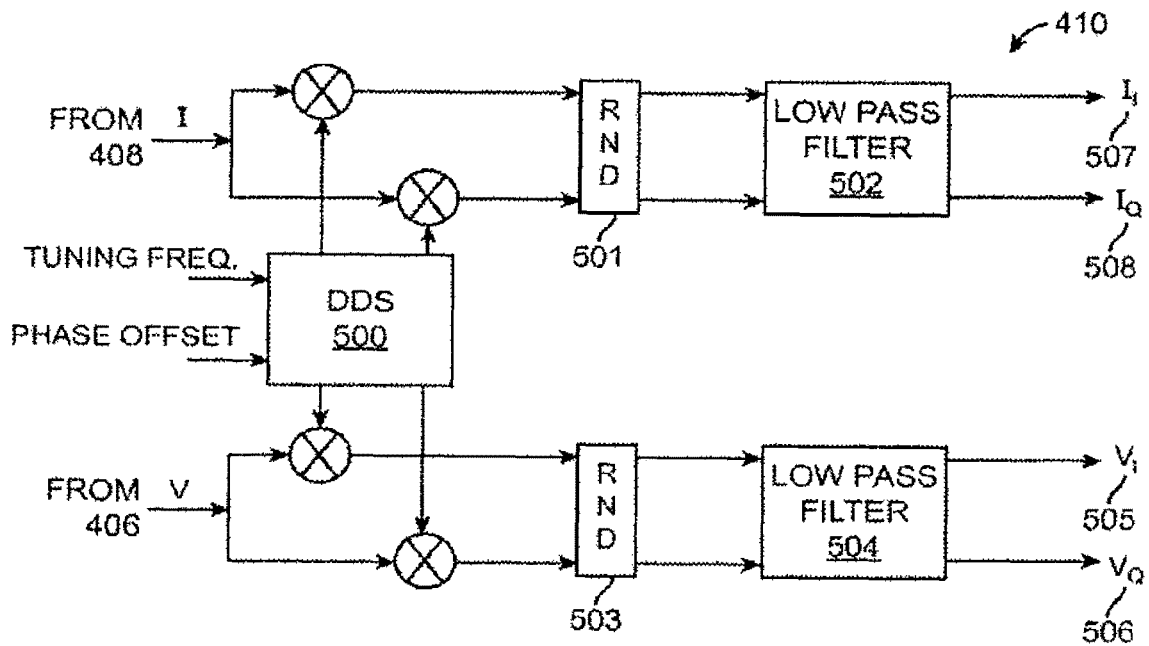
FIG. 5 schematically illustrates one embodiment of a DDS down conversion section of a peak effective power sensor block shown in FIG. 4.
Figure 6:
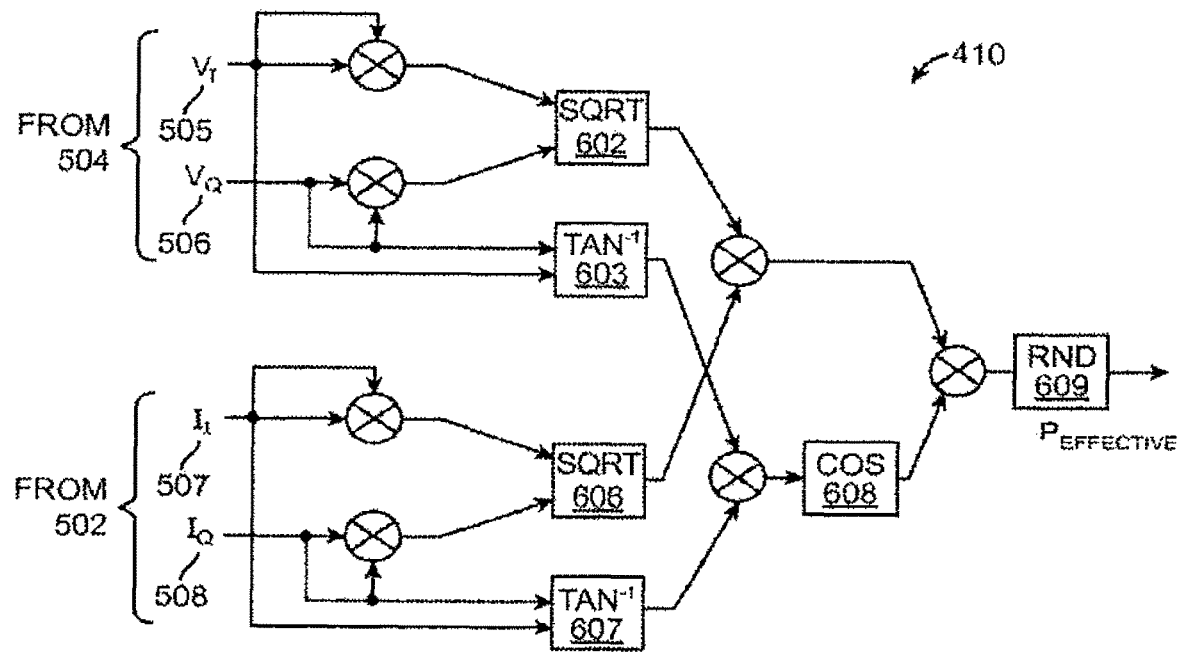
FIG. 6 schematically illustrates one embodiment of the DC baseband processing section of a peak effective power sensor block shown in FIG. 4.

In a preferred embodiment shown in FIGS. 5 and 6, the peak effective power sensor block 410 may comprise a DDS 500 used to mix voltage sense signal V (from 406) and current sense signal I (from 408) down to DC baseband signals, preferably generating a voltage output with low-pass filter 502, and a current output with low-pass filter 504. The voltage and current output from peak effective power sensor block 410 include in-phase current 507, in-phase voltage 505, and quadrature current 508, quadrature voltage 506 components. It is preferable for signals within the circuit 410 to comprise in-phase and quadrature components because blocks within the circuit 410 may then recognize the instantaneous amplitude, frequency, and phase shift between the components of a signal and between the several signals passing through the blocks of circuit 410. The digital output signals from low-pass filter 502 and low-pass filter 504 of peak effective power sensor 410 may then be transmitted to the power calculation circuits shown in FIG. 6.

Now referring to FIG. 6, voltage amplitude may be calculated by summing the squares of the in-phase voltage signal 505 and the quadrature voltage signal 506, and passing the sum through square root circuit 602. Current amplitude may be calculated by summing the squares of the in-phase current signal 507 and the quadrature current signal 508, and passing the sum through square root circuit 606. Uncorrected power may preferably be calculated by multiplying voltage amplitude and current amplitude.

The phase of the voltage signal may preferably be calculated by passing the quadrature component 506 of the voltage signal and the in-phase component 505 of the voltage signal through inverse tangent gate 603. Similarly, the phase of the current signal may preferably be calculated by passing the quadrature component 508 of the current signal and the in-phase component 507 of the current signal through inverse tangent gate 607. Cosine gate 608 preferably receives the difference output from inverse tangent gates 603 and 607 such that a power factor correction may be calculated. The peak effective power may be calculated by multiplying the uncorrected power by the output of the cosine gate 608 and rounding the result with rounding gate 609.

Although FIGS. 5 and 6 represent a most preferred embodiment, peak effective power may be calculated using other means, such as multiplying the instantaneous RF voltage and RF current waveforms together and integrating the resulting signal to obtain an average value; the means for calculating peak effective power being selected from any available means suitable for the type of power used and suitable for the components comprising the circuitry of the apparatus disclosed and described herein.

Figure 9A:
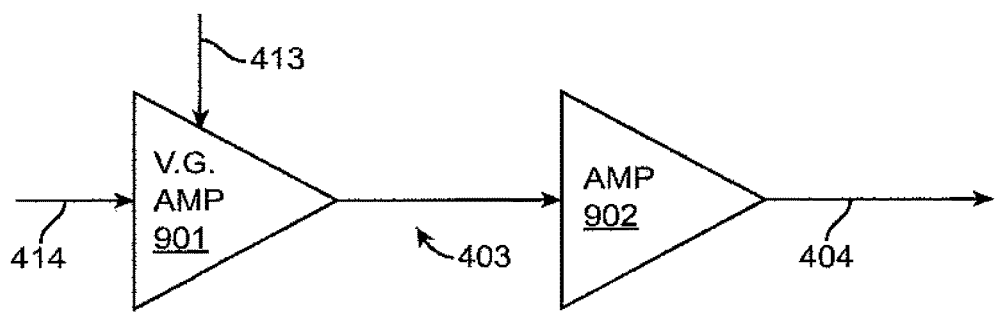
FIG. 9A schematically illustrates one embodiment of the amplifier block shown in FIG. 4.
Figure 9B:
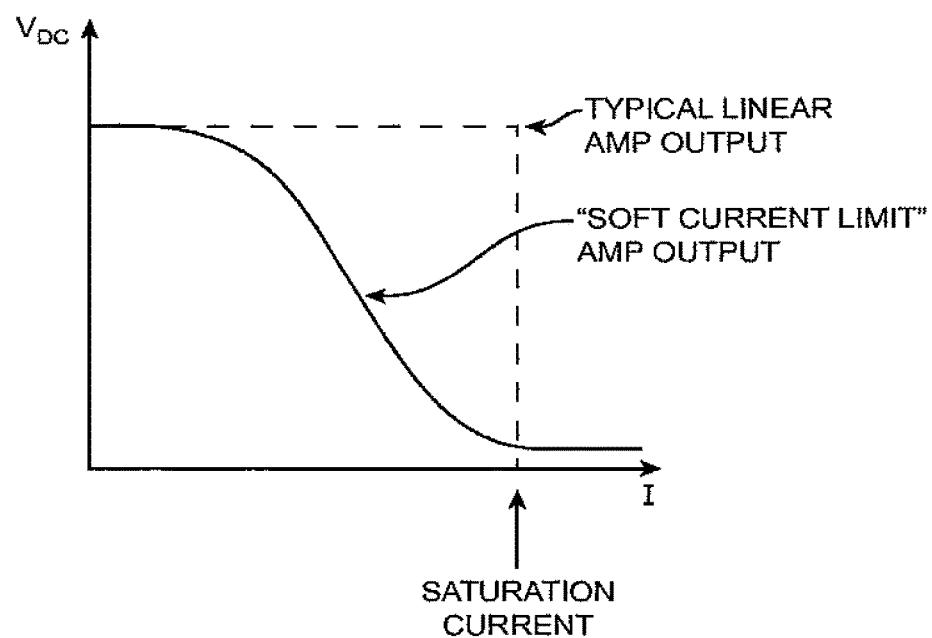
FIG. 9B illustrates the "soft current limit" relationship for the amplifier block shown in FIG. 4.
Figure 10:
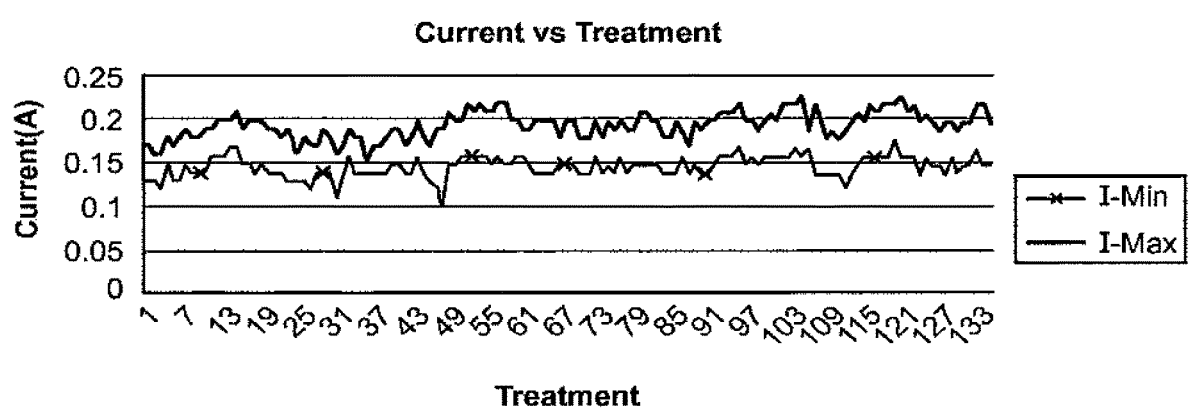
FIG. 10 is an exemplary plot of maximum and minimum measured current in a tissue treatment embodiment of the apparatus shown in FIG. 1.
Figure 11:
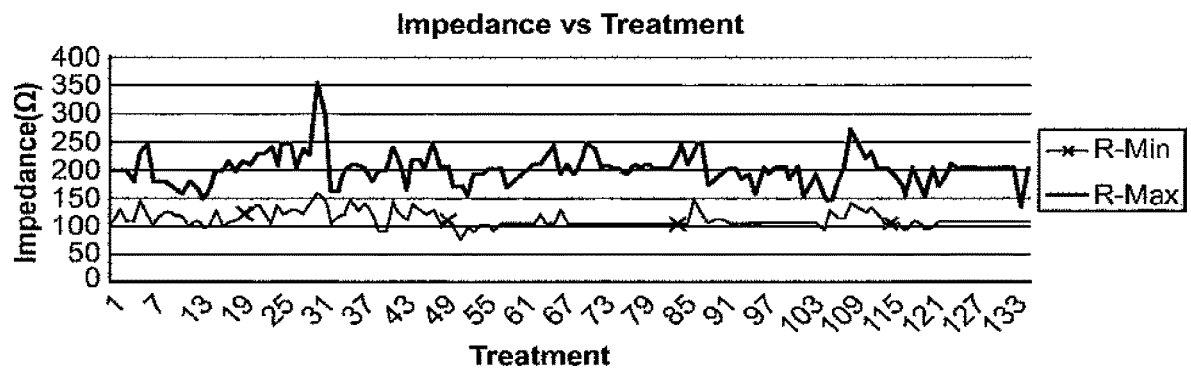
FIG. 11 is an exemplary plot of maximum and minimum measured impedance in a issue treatment embodiment of the apparatus shown in FIG. 1.
Figure 12:
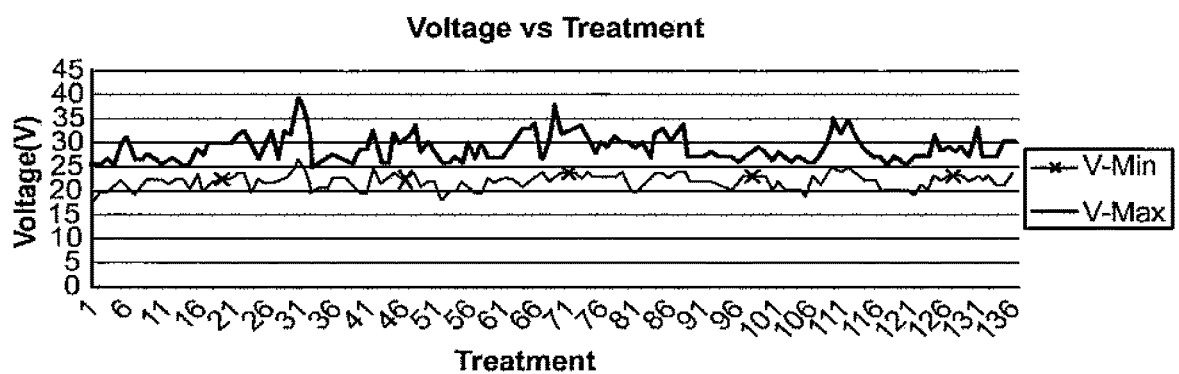
FIG. 12 is an exemplary plot of maximum and minimum measured voltage in a tissue treatment embodiment of the apparatus shown in FIG. 1.

Now referring to FIGS. 9A and 9B, amplifier block 403 may include variable gain amplifier 901, receiving voltage input 414 from DDS block 400 and modulating voltage signal 413 from PID controller 411, and power amplifier 902. Power amplifier 902 has a "soft current limit" as shown in FIG. 9B, whereby the available output voltage decreases in a tailored manner as the required output current is increased. The advantage of power amplifier 902 having a soft current limit is that the maximum output power delivered can be inherently limited by the characteristic of the current limit circuit, wherein the current limit circuit may provide a substantially constant maximum available output power across a broad range of load impedances, most preferably exceeding about a decade of load impedance. An additional advantage of the soft current limit scheme is that, when implemented using switched mode power supply technology, extremely high power amplifier efficiencies can be achieved across a broad range of load impedances, preferably exceeding about a decade of load impedance.

Control of target power output 404 may be preferably achieved through power set point control 409, and peak effective power sensor block 410 passing signals to PID controller 411 that may ultimately produce modulating voltage signal 413 passing into amplifier block 403. Power output set point control 409 may provide a software control signal based on programmed operating parameters, which in many embodiments may be set to promote remodeling of diseased tissue in a manner that avoids damage to surrounding healthy tissue. By taking real-time load measurements in-phase and in quadrature at power output 404, circuit 400 is thereby able to characterize and respond to load variations by modulating output such that output may vary within a relatively small range from set point. Power output variation about the set point may be about ±2%, however, preferred embodiments may regulate output variation in other ranges, such as, about ±5%, about ±10%, about ±15%, and about ±20% or greater.

Figure 7:
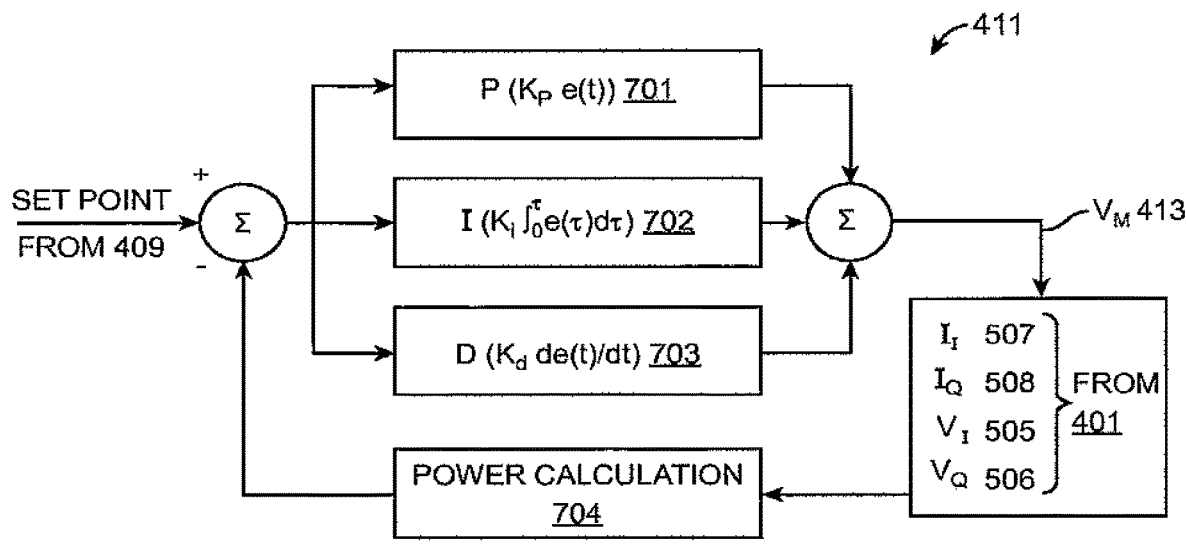
FIG. 7 schematically illustrates one embodiment of a PID control block shown in FIG. 4.

Now referring to FIGS. 4 and 7, PID controller 411 preferably receives output signals from power output set point 409 and peak effective power output block 410. PID controller 411 may comprise hardware and or software modules which perform proportional 701 ("P"), integral 702 ("I"), and derivative 703 ("D") calculations $K_p e(t)$, $K_i \int_0^\tau e(\tau)d\tau$, and $K_d de(\tau)/dt$, respectively, which may be expressed in the ideal form of the equation $V_m(t)=K_p e(t)+K_i \int_0^\tau e(\tau)d\tau+K_d de(\tau)/dt$, where, $V_m(t)$ represents the computed modulating voltage 413 as a function of time in response to measured power at the output 404, the peak effective power calculation 410, and power set point 409.

Wherein:

$K_p e(t)$ represents the proportional reaction to error in the measured/calculated power to the desired power;

$K_i \int_0^\tau e(\tau)d\tau$ represents the integral reaction to the sum of the errors in the measured/calculated power to the desired power, where τ represents the period of time integrated over and e(t) represents the calculated power at the present time t; and, $K_d de(\tau)/dt$ represents the derivative reaction to the rate of change in the error of the measured/calculated power to the desired power.

In the most preferred embodiment, the PID equation may be expressed in the more common "standard" or "industrial" form $V_m(t)=K_p[e(t)+1/T_i \int_0^\tau e(\tau)d\tau+T_d de(\tau)/dt]$, where, constants $K_i$ and $K_d$ are replaced with $T_i$ and $T_d$, representing the integral and derivative time values respectively. The standard form provides the advantage of simplifying the derivation and use of constants in the control equation.

In a preferred embodiment, time interval "t" of about 160 microseconds exists between power measurements and calculations of power at the target power output 404. The output calculation of the PID control loop of 411 may be referred to as the "manipulated variable" or modulating voltage 414 that is preferably used to drive amplifier block 403 to regulate output power closely about a set point. The constants $K_i$, $K_p$, and $K_d$ help to define how quickly circuit 400 may respond to increasing errors in output 404, or how quickly to modulate amplifier block 403 to reduce error in output at 404 as compared to set point 409. The power calculation 704 is preferably based on the quadrature 506 and in-phase 505 voltage components, and the quadrature 507 and in-phase 508 current components of the output of DDS block 401.

Figure 8:
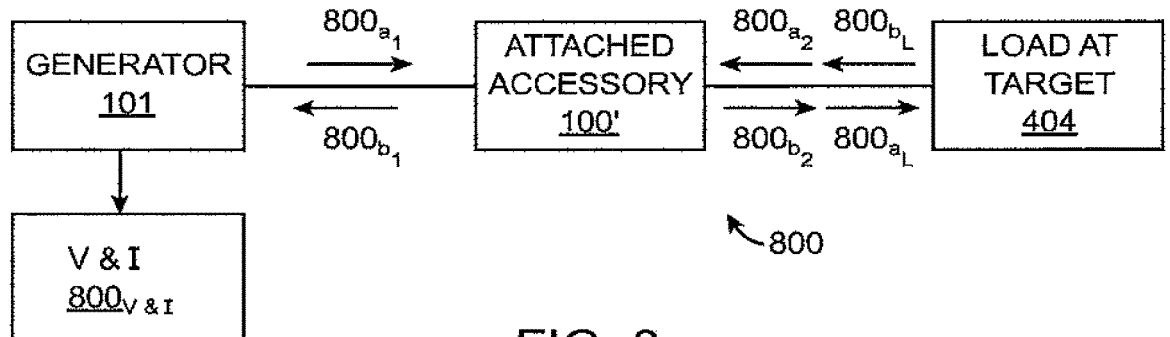
FIG. 8 schematically illustrates a two-port network design for sensing and controlling incident and reflected power.

Now referring to FIGS. 1 and 8, the overall apparatus 100, which includes both the power generator and control apparatus of enclosure 101 and an attached accessory 100' (which, for example, may comprise the catheter assembly 108 and connector 103 of FIG. 1), may utilize a communication schema such as that shown in FIG. 8. Although FIG. 8 depicts a preferred embodiment utilizing a two-port network 800, other numbers of communication ports may be employed depending on the desired arrangement for a given power control application. In general there are usually significant RF losses, reflections and phase shifts between voltage sensor 405, current sensor 407 and the target load (tissue) 404. These RF losses, reflections and phase shifts cause significant deviations in the actual power delivered to the load (tissue) 404 and additionally cause significant errors in the measurement of load (tissue) impedance. In a preferred embodiment, generalized 2-port reflectometry is used to compensate for all the RF losses, reflections and phase shifts in the RF path, both with respect to accurately controlling load (tissue) power and accurately measuring load (tissue) impedance. For this purpose, the two-port network 800 may comprise a series of control computations utilizing incident and reflected power waves between power generator and control apparatus of enclosure 101, attached accessory 100', and the load at the target power output 404, preferably resulting in controlled voltage and current output 800V&I by power generator and control apparatus of enclosure 101.

Incident power waves are denoted by subscript "$a_n$", reflected power waves are denoted by subscript "$b_n$", incident and reflected power at 404 are denoted by "$a_L$" and "$b_L$" respectively. For the purpose of clarity in the following description of the mathematic operations represented in FIG. 8, mathematic equations shall omit the descriptive element number "800" shown in FIG. 8 to simplify the meaning of the equations described.

The two-port network definition of scattering parameters in terms of incident and reflected power waves ($a_n$ and $b_n$, respectively) are defined as:

$$a_1 = \frac{1}{2}\left(\frac{V_1}{\sqrt{Z_o}} + I_1\sqrt{Z_o}\right). \quad\quad 1$$

$$b_1 = \frac{1}{2}\left(\frac{V_1}{\sqrt{Z_o}} - I_1\sqrt{Z_o}\right). \quad\quad 2$$

$$a_2 = \frac{1}{2}\left(\frac{V_2}{\sqrt{Z_o}} + I_2\sqrt{Z_o}\right). \quad\quad 3$$

$$b_2 = \frac{1}{2}\left(\frac{V_2}{\sqrt{Z_o}} - I_2\sqrt{Z_o}\right). \quad\quad 4$$

Wherein, a1 and b1 are the incident and reflected power waves at generator 101, and $a_2$ and $b_2$ are the incident and reflected power waves at the load (electrodes 112, for example).

The S-Parameter matrix for the two-port network along with expanded equations may be defined as:

$$\begin{pmatrix}b_1\\b_2\end{pmatrix} = \begin{pmatrix}S_{11} & S_{12}\\S_{21} & S_{22}\end{pmatrix}\begin{pmatrix}a_1\\a_2\end{pmatrix}. \quad\quad 5$$

$$b_1 = S_{11}a_1 + S_{12}a_2. \quad\quad 6$$

$$b_2 = S_{12}a_1 + S_{22}a_2. \quad\quad 7$$

The complex impedances at the generator 101, which may comprise circuit 400, and at the load 404 may be respectively defined as rho ($\rho$) and gamma ($\Gamma$). Rho and gamma preferably may then be defined using the incident and reflected power waves as:

$$\rho = \frac{b_1}{a_1}. \quad\quad 8$$

$$\Gamma = \frac{a_2}{b_2}. \quad\quad 9$$

The reverse transform from rho space to gamma space may now be derived using the relationships in Equations 1 through 9, as shown below:

$$\frac{1}{\Gamma} = \frac{b_2}{a_2} = S_{22} + \frac{S_{12}a_1}{a_2}. \quad\quad 10$$

$$\frac{1}{\Gamma} - S_{22} = \frac{S_{12}a_1}{a_2}. \quad\quad 11$$

$$\frac{1}{\frac{1}{\Gamma} - S_{22}} = \frac{a_2}{S_{12}a_1}. \quad\quad 12$$

$$\frac{a_2}{a_1} = S_{12}\left(\frac{1}{\frac{1}{\Gamma} - S_{22}}\right). \quad\quad 13$$

$$p = \frac{b_1}{a_1} = S_{11} + \frac{S_{12}a_2}{a_1}. \quad\quad 14$$

$$p = S_{11} + S_{12}^2\left(\frac{\Gamma}{1 - S_{22}\Gamma}\right). \quad\quad 15$$

$$p = S_{11} + S_{12}^2\left(\frac{\Gamma}{1 - S_{22}\Gamma}\right). \quad\quad 16$$

$$p = \frac{S_{11}(1 - S_{22}\Gamma) + S_{12}^2\Gamma}{1 - S_{22}\Gamma}. \quad\quad 17$$

$$p = \frac{S_{11} + (S_{12}^2 - S_{11}S_{22})\Gamma}{1 - S_{22}\Gamma}. \quad\quad 18$$

Equation 18 provides the explicit form of the reverse transform from rho space to gamma space. The scattering parameters may be grouped and preferably defined as reverse transform coefficients A, B, and D in the following form:

$$A = s_{11} \quad\quad 19.$$

$$B = s_{12}^2 - s_{11}s_{22} \quad\quad 20.$$

$$D = -s_{22} \quad\quad 21.$$

Equation 18 may be simplified by substituting coefficients A, B, and D into the preferred explicit form of the reverse transform, thereby providing a preferred general form of the reverse transform:

$$\rho = \frac{A + B\Gamma}{1 + D\Gamma}. \quad\quad 22$$

Using Equation 22, and solving for gamma, the forward transform may be derived in preferred form:

$$\rho = D\Gamma\rho = A + B\Gamma. \quad\quad 23$$

$$D\Gamma\rho - B\Gamma = A - \rho. \quad\quad 24$$

$$\Gamma(D\rho - B) = A - \rho. \quad\quad 25$$

$$\Gamma = \frac{A - \rho}{D\rho - B}. \quad\quad 26$$

$$\Gamma = \frac{\left(-\frac{A}{B}\right) + \frac{1}{B}\rho}{1 + \left(-\frac{D}{B}\right)\rho}. \quad\quad 27$$

In a similar fashion as Equations 19 through 21, forward transform coefficients A', B', and D' may preferably serve to simplify the equation between gamma and rho space as shown:

$$A' = \left(-\frac{A}{B}\right) \quad 28$$

$$B' = \left(\frac{1}{B}\right) \quad 29$$

$$D' = \left(-\frac{D}{B}\right) \quad 30$$

Equation 12 may be simplified by substituting coefficients A', B', and D' into the preferred explicit form of the forward transform, thereby providing a preferred general form of the forward transform:

$$\Gamma = \frac{A' + B'\rho}{1 + D'\rho}. \quad 31$$

Forward power at the load 404 may be preferably defined as the magnitude of the square of the power wave incident on load 404:

$$P_{FL} = |a_L|^2 = |b_2|^2 \quad 32.$$

Similarly, the reverse power from load 404 may be defined as the magnitude of the square of the power wave reflected by load 404:

$$P_{RL} = |b_L|^2 = |a_2|^2 \quad 33.$$

Through the relationships defined above, the power absorbed at the target power output load 404, may be defined as incident power minus reflected power through the relationships:

$$P_L = P_{AL} - P_{RL}. \quad 34$$

$$P_L = |a_L|^2 - |b_L|^2. \quad 35$$

$$P_L = |a_L|^2 \left\{1 - \frac{|b_L|^2}{|a_L|^2}\right\}. \quad 36$$

and, substituting Equations 7, 9, and 32 into Equations 34 through 36, provides the expanded form of the relationships:

$$P_L = |a_L|^2 \{1 - |\Gamma|^2\} \quad 37.$$

$$P_L = P_{FL} \{1 - |\Gamma|^2\} \quad 38.$$

$$P_L = |b_2|^2 (1 - |\Gamma|^2) \quad 39.$$

$$P_L = |s_{21}a_1 + s_{22}a_2|^2 (1 - |\Gamma|^2) \quad 40.$$

In the most preferred two-port network, incident and reflected power at port 1 may now be defined. Incident power at $800_{a1}$ may preferably be defined as the magnitude of the square of the power wave incident at $800_{a1}$:

$$P_{F1} = |a_1|^2 \quad 41.$$

and, reflected power at $800_{b1}$ may preferably be defined as the magnitude of the square of the power wave reflected at $800_{b1}$:

$$P_{R1} = |b_1|^2 \quad 42.$$

Power absorbed at port 1 ("$P_1$") may be defined, using Equations 41 and 42, as the incident power at port 1 minus the reflected power at port 1:

$$P_1 = |a_1|^2 - |b_1|^2 = |a_1|^2 (1 - |\rho|^2) \quad 43.$$

which, may also be defined as the magnitude of the absorbed voltage multiplied by the magnitude of the absorbed current multiplied by the cosine of the angle between the absorbed voltage and absorbed current:

$$P_1 = |V||I|\cos\phi| = |a_1|^2 (1 - |\rho|^2). \quad 44$$

$$|a_1|^2 = \frac{|V||I|\cos\phi|}{(1 - |\rho|^2)}. \quad 45$$

Substituting Equation 9 into Equation 7 and solving for $b_2$ may define the following relationships defined for $800_{b2}$ in FIG. 8:

$$b_2 - S_{22}a_2 = S_{12}a_1. \quad 46$$

$$b_2 \left(1 - S_{22}\frac{a_2}{b_2}\right) = S_{12}a_1. \quad 47$$

$$b_2 (1 - S_{22}\Gamma) = S_{12}a_1. \quad 48$$

$$b_2 = \frac{S_{12}a_1}{(1 - S_{22}\Gamma)}. \quad 49$$

The power at load 404 in FIG. 8 may now be defined by substituting Equation 49 into Equation 39 and expanding the numerator by substituting Equation 45 into Equation 51:

$$P_L = \left|\frac{S_{12}a_1}{(1 - S_{22}\Gamma)}\right|^2 (1 - |\Gamma|^2). \quad 50$$

$$P_L = \frac{|S_{12}|^2 |a_1|^2}{|(1 - S_{22}\Gamma)|^2} (1 - |\Gamma|^2). \quad 51$$

$$P_L = \frac{|S_{12}|^2 |V||I|\cos\phi|(1 - |\Gamma|^2)}{(1 - |\rho|^2)|(1 - S_{22}\Gamma)|^2}. \quad 52$$

Figure 16:
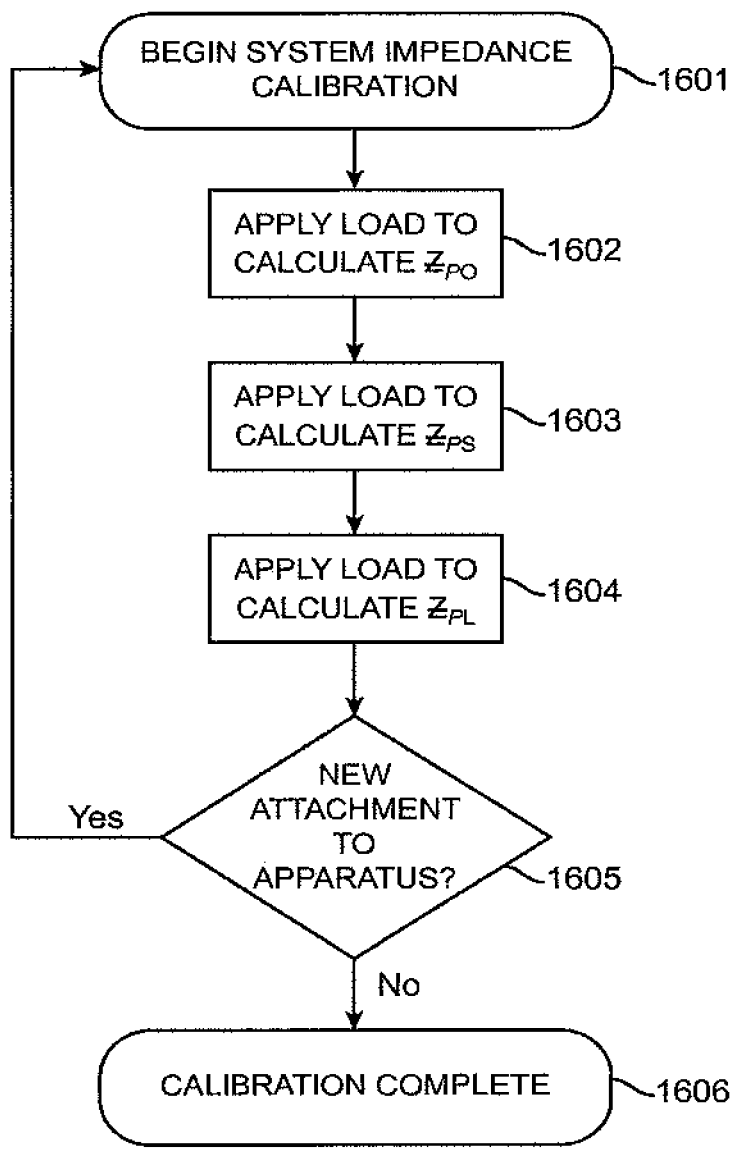
FIG. 16 schematically illustrates a method and system for calibrating a power generating system so as facilitate accurate measurement of impedance at a target power output.

In a preferred embodiment of the present invention, measurement of known impedances in circuit 400 of FIG. 4 may be made in order to define the transform coefficients A, B, D and A', B', D', as can be understood with reference to FIG. 16. Most preferably, three measurements are taken at known circuit loads 404, most preferably, impedance $Z_{\rho O}$ is taken at load of about 1000Ω, impedance $Z_{\rho S}$ is taken at a load of about 50Ω, and impedance $Z_{\rho L}$ is taken at a load of about 150Ω, where the complex voltage and current measurements ($800_{V\&1}$ of FIG. 8) at power generator and control apparatus 101 are used to calculate impedances $Z_{\rho O}$, $Z_{\rho S}$, and $Z_{\rho L}$ using Equation 53 where SYSTEM$_{IMPEDANCE}$ is assigned the value 150Ω. However, known circuit loads and assigned SYSTEM$_{IMPEDANCE}$ to compute $Z_{\rho O}$, $Z_{\rho S}$, and $Z_{\rho L}$ may be performed at other values ranging between about zero Ohms and about infinite Ohms. As shown in FIG. 16, such a calibration method may begin 1601 prior to coupling of the power generation components to the target tissue, and ideally before coupling of attachment 100' to the power generation circuit 400 of enclosure 101. Three differing loads are applied with impedances being taken 1602, 1603, and 1604 at each load. These measurements are taken with the components of circuit 400, and are input into a hardware and/or software module for the system characterization calculations described herein.

$$Z_{\rho N} = \frac{\left(\frac{V_N}{I_N} - SYSTEM_{IMPEDANCE}\right)}{\left(\frac{V_N}{I_N} + SYSTEM_{IMPEDANCE}\right)}. \qquad 53$$

Solving Equation 53 may preferably involve a preliminary set of impedance measurements most preferably using network analysis, most preferably vector network analysis, to preferably provide impedances $Z_{\Gamma O}$, $Z_{\Gamma S}$, and $Z_{\Gamma L}$ at the respective loads of about 1000Ω, about 50Ω, and about 150Ω. The six preferred impedance measurements $Z_{\Gamma O}$, $Z_{\Gamma S}$, $Z_{\Gamma L}$, $Z_{\rho O}$, $Z_{\rho S}$, and $Z_{\rho L}$ may then preferably be used to calculate the transform coefficients A', B', D':

$$D' = \frac{(Z_{\Gamma S} - Z_{\Gamma O})*(Z_{\rho O} - Z_{\rho L}) - (Z_{\Gamma O} - Z_{\Gamma L})*(Z_{\rho S} - Z_{\rho O})}{(Z_{\Gamma O} * Z_{\rho O} - Z_{\Gamma S} * Z_{\rho S})*(Z_{\rho O} - Z_{\rho L}) - (Z_{\Gamma L} * Z_{\rho L} - Z_{\Gamma O} * Z_{\rho O})*(Z_{\rho S} - Z_{\rho O})} \qquad 54$$

$$B' = \frac{Z_{\Gamma O} - Z_{\Gamma L} - D*(Z_{\Gamma L}*Z_{\rho L} - Z_{\Gamma O}*Z_{\rho O})}{(Z_{\rho O} - Z_{\rho L})} \qquad 55$$

$$A' = Z_{\Gamma S} - B*Z_{\rho S} + D*(Z_{\Gamma S}*\Gamma_{\rho S}) \qquad 56$$

The value of the coefficients preferably defined by Equations 54 through 56 may now be preferably used to calculate actual load impedances at target power output 404 of FIG. 4 using Equation 31, and the actual power applied at target power output 404 using Equation 52, thereby preferably providing a calculated modulating output voltage 413 from PID controller 411 such that output at 404 is accurately regulated about a set point based on real-time changes in load, and power delivery is maintained within a range as described herein.

In preferred embodiments actual power output at the power delivery point is most preferably based on measured complex impedance angle of applied load at output 404. Wherein, the load most preferably denotes tissue and the complex impedance angle preferably denotes the health or disease of tissue and/or the change in tissue state through the course of the use of apparatus 100. Furthermore, because impedance is a function of capacitance and resistance, real-time tissue capacitance and real-time tissue resistance may also be known based on measured data through the relationship between impedance, capacitance, and resistance:

$$Z = (SYSTEM_{IMPEDANCE}) * \frac{(1+\Gamma)}{(1-\Gamma)}. \qquad 57$$

Recalling that impedance may have real and imaginary components, the relationship in Equation 57 may be further expressed and developed as follows:

$$Z = \frac{1}{\left(\frac{1}{R} + j\omega C\right)}. \qquad 58$$

$$Z = \frac{1}{\left(\frac{1}{R} + j\omega C\right)} * \frac{(1 - j\omega CR)}{(1 - j\omega CR)}. \qquad 59$$

-continued $$Z = \frac{R - j\omega CR^2}{(1 + \omega^2 C^2 R^2)}. \qquad 60$$

$$Z_{REAL} = \frac{R}{(1 + \omega^2 C^2 R^2)}. \qquad 61$$

$$Z_{IMAGINARY} = \frac{-j\omega CR^2}{(1 + \omega^2 C^2 R^2)}. \qquad 62$$

where ω denotes the natural frequency of the circuit, C denotes real-time tissue capacitance as measured at the load, and R denotes real-time tissue resistance as measured at the load.

Solving Equation 61 for $C^2$ and substituting Equation 63 into Equation 62, and solving Equation 64 for C:

$$C^2 = \frac{R - Z_{REAL}}{(\omega^2 R^2 Z_{REAL})}. \qquad 63$$

$$Z_{IMAGINARY} = \frac{-j\omega CR^2}{\left(1 + \omega^2 R^2 * \frac{(R - Z_{REAL})}{(\omega^2 R^2 Z_{REAL})}\right)}. \qquad 64$$

$$C = \frac{-Z_{IMAGINARY}}{Z_{REAL}\omega R}. \qquad 65$$

By solving Equation 65 for $\omega^2 C^2 R^2$ and substituting into Equation 61, the simplified relationship may be obtained:

$$Z_{REAL} = \frac{R}{\left(1 + \frac{Z_{IMAGINARY}}{Z_{REAL}}\right)}. \qquad 66$$

Now, the real-time tissue resistance may be determined through the known value of impedance Z from Equation 57 by simplifying Equation 66 and solving for R:

$$R = Z_{REAL} * \left(1 + \left(\frac{Z_{IMAGINARY}}{Z_{REAL}}\right)^2\right). \qquad 67$$

and real-time tissue capacitance may be determined by substituting Equation 67 into Equation 65 and solving for C:

$$C = \frac{-Z_{IMAGINARY}}{Z_{REAL}^2 \omega \left(1 + \left(\frac{Z_{IMAGINARY}}{Z_{REAL}}\right)^2\right)}. \qquad 68$$

In the most preferred embodiments of the system or overall apparatus 100 of FIG. 1 may include circuit 400 of FIG. 4 and coupling apparatus or accessory 100', which may together be employed in the characterization and selective treatment of tissue to promote a therapeutic response. The characterization and selective treatment of tissue based on impedance, imaging modalities, and energy modalities are described by U.S. Pat. No. 7,291,146 to Steinke, et al., issued on Nov. 6, 2007, entitled "Selectable Eccentric Remodeling and/or Ablation of Atherosclerotic Material", and the above referenced U.S. application Ser. Nos. 11/392,231, 11/975,651, 11/617,519, 11/975,474, 11/975,383, 12/564,268, the full disclosures of which are incorporated herein by reference. In the most preferred embodiments, power output is RF energy, however, ultrasound, laser, microwave, and the like as disclosed and described in the preceding references, are also within the scope of the present invention.

Now referring to FIG. 4, in some embodiments DDS block 401, power output set point control 409, and peak effective power sensor block 410 comprise a field programmable gate array without an embedded processor. In other embodiments where a field programmable gate array comprises an internal processor, DDS block 401, power output set point control 409, peak effective power sensor block 410, and PID controller may be comprised within the field programmable gate array.

In some embodiments, generator and control apparatus 101 may include a processor or be coupled to a processor to control or record treatment. The processor will typically comprise computer hardware and/or software, often including one or more programmable processor units running machine readable program instructions or code for implementing some, or all of, one or more of the embodiments and methods described herein. The code will often be embodied in a tangible media such as a memory (optionally a read only memory, a random access memory, a non-volatile memory, or the like) and/or a recording media (such as a floppy disk, a hard drive, a CD, a DVD, a non-volatile solid-state memory card, or the like). The code and/or associated data and signals may also be transmitted to or from the processor via a network connection (such as a wireless network, an ethernet, an internet, an intranet, or the like), and some or all of the code may also be transmitted between components of a catheter system and within the processor via one or more bus, and appropriate standard or proprietary communications cards, connectors, cables, and the like will often be included in the processor. The processor may often be configured to perform the calculations and signal transmission steps described herein at least in part by programming the processor with the software code, which may be written as a single program, a series of separate subroutines or related programs, or the like. The processor may comprise standard or proprietary digital and/or analog signal processing hardware, software, and/or firmware, and may preferably have sufficient processing power to perform the calculations described herein during treatment of the patient, the processor optionally comprising a personal computer, a notebook computer, a tablet computer, a proprietary processing unit, or a combination thereof. Standard or proprietary input devices (such as a mouse, keyboard, touchscreen, joystick, etc.) and output devices (such as a printer, speakers, display, etc.) associated with modern computer systems may also be included, and processors having a plurality of processing units (or even separate computers) may be employed in a wide range of centralized or distributed data processing architectures.

In the most preferred embodiments control software for apparatus 100 may use a client-server schema to further enhance system ease of use, flexibility, and reliability. "Clients" are the system control logic; "servers" are the control hardware. A communications manager delivers changes in system conditions to subscribing clients and servers. Clients "know" what the present system condition is, and what command or decision to perform based on a specific change in condition. Servers perform the system function based on client commands. Because the communications manager is a centralized information manager, new system hardware preferably may not require changes to prior existing client-server relationships; new system hardware and its related control logic may then merely become an additional "subscriber" to information managed through the communications manager. This control schema preferably provides the benefit of having a robust central operating program with base routines that are fixed; preferably no change to base routines may be necessary in order to operate new circuit components designed to operate with the system.

Accessories for Tissue Treatment

In some embodiments, the overall system or apparatus 100 of FIG. 1 may, along with the power generation apparatus, further include attached accessories, which most preferably may include an intraluminal catheter 108 having an energy delivery surface comprised therein.

In many embodiments, an energy delivery surface may preferably comprise a plurality of spaced electrodes 112. The power generating apparatus 101 as shown in FIG. 1 is operatively coupled to the plurality of electrodes by connector 103 so as to preferably allow the selective energizing of selected electrodes.

Figure 3A:
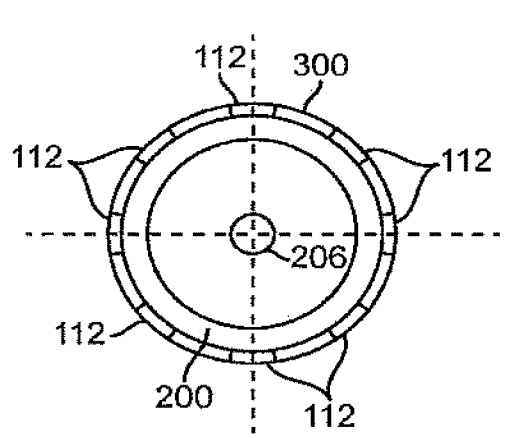
FIG. 3A schematically illustrates a cross-sectional view of the balloon of FIG. 2.

In many embodiments, the energy delivery surface comprises a plurality of electrodes 112 disposed about an expandable balloon 200, as shown in FIG. 3A, so as to define a plurality of remodeling zones in the target tissue when the balloon is expanded to come in contact with tissue such as that of a lumen.

Figure 2:
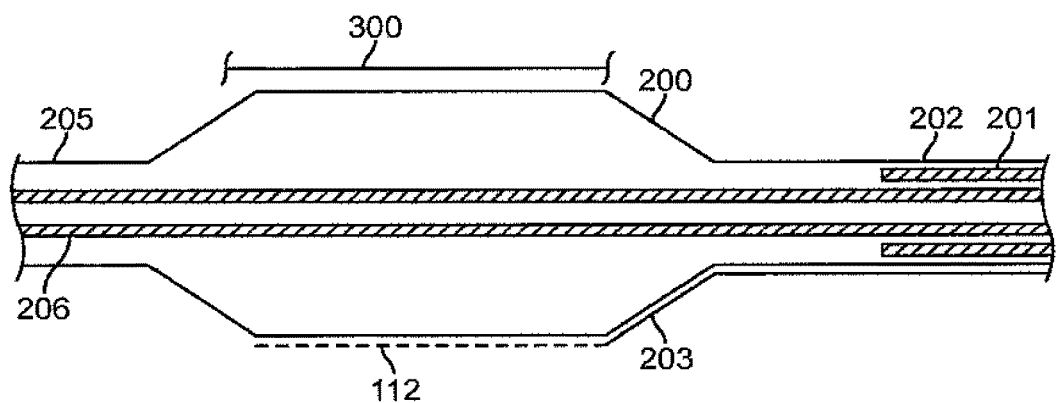
FIG. 2 schematically illustrates one embodiment of an inflatable balloon for use in the apparatus of FIG. 1.

Now referring to FIGS. 1 and 2, one exemplary embodiment of a catheter system inducing desirable temperature effects on tissue is shown. The catheter system includes a balloon catheter 108 having a catheter body 109 with a proximal end 107 and a distal end 111. Catheter body 109 is flexible and defines a catheter axis 113, and may include one or more lumens, such as a guidewire lumen 206 and an inflation lumen 201. Still further lumens may be provided if desired for other treatments or applications, such as perfusion, fluid delivery, imaging, or the like. Catheter 108 includes an inflatable balloon 200 adjacent distal end 111 and a housing 106 adjacent proximal end 107. Housing 106 includes a first connector 104 in communication with guidewire lumen 206 and a second connector 105 in fluid communication with inflation lumen 201. Inflation lumen 201 extends between balloon 200 and second connector 105. Both first and second connectors 104 and 105 may optionally comprise a standard connector, such as a LUER-LOC™ connector. A distal tip may include an integral tip valve to allow passage of guidewires, and the like.

Figure 3B:
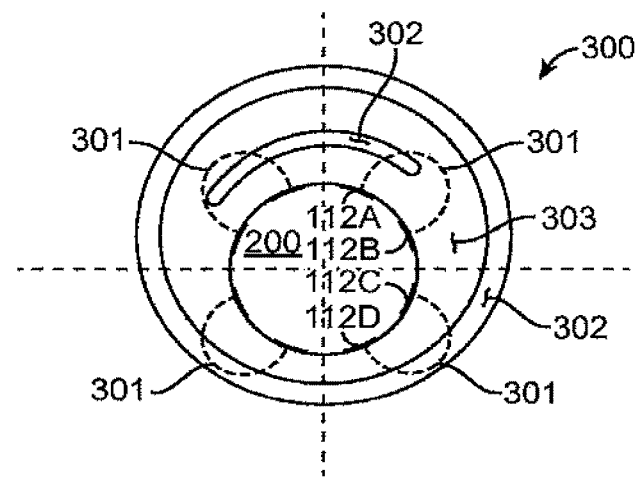
FIG. 3B schematically illustrates one embodiment of electrodes for use in tissue analysis and selective energy treatment using the apparatus of FIG. 1.

The housing 106 may also accommodate an electrical connector 103, which may preferably include a plurality of electrical connections, each electrically coupled to electrodes 112 via conductors 203. This arrangement preferably allows the electrodes 112 to be easily energized, the electrodes often being energized by an enclosed controller and power source 101, which may preferably produce energy in the form of monopolar or bipolar RF energy, microwave energy, ultrasound energy, or other such suitable forms of energy. In one such embodiment, the electrical connector 103 is coupled to circuit 400 of FIG. 4 that in its most preferable form may produce RF energy in a manner that may allow energy to be selectively directed to electrodes 112 as shown in FIG. 3B. When monopolar RF energy is employed, patient ground may, for example, be provided by an external electrode or an electrode on catheter body 109.

Now referring to FIGS. 3B and 1, the electrodes 112 are preferably coupled with the surrounding tissue 300, such that energy may be transmitted between the electrodes 112A, 112B, 112C, 112D and the tissue 300 so as to preferably initiate a biological response. The balloon 200 will typically comprise distal end 111 of a balloon catheter 108, and the energy delivery surfaces, such as electrodes 112, on the balloon 200 will generally be energized using an energy source coupled to proximal end 107 of catheter 108. An energy conduit 203 may extend along a catheter body 109 between the proximal end 107 and balloon 200, with the energy conduit 203 often comprising an electrical conductor for applying RF energy or the like, a light conductor such as a fiber optic filament running along a lumen in the catheter body so as to conduct laser or other light energies, or the like.

As shown in FIG. 3B, electrodes 112 may preferably be positioned circumferentially around balloon 200. Energy 301, most preferably RF energy, may in the most preferred embodiment be directed to adjacent pairs of electrodes 112A and 112C, or 112A and 112D, or any combination of electrodes 112A-112D, treating both the healthy portion of tissue 303 and diseased portion of tissue 302 within the surrounding tissue 300. This arrangement preferably creates an energy path 301 that may deliver energy or heat ("tissue remodeling energy") in particular treatment zones or segments to the tissue 300 between the electrode pairs 112A-112D ('remodeling zones") having a volume between the electrode pairs 112A-112D at a specific depth. Using different combinations of electrode pairs 112A-112D may reduce or eliminate gaps between the remodeling zones by using overlapping pairs. Using electrode pairs 112A-112D with bipolar energy preferably may thereby provide improved performance compared to a monopolar approach. Diseased tissue 302 is known to have higher electrical resistivity than healthy tissue 303. By using pairs of electrodes 112 in a bipolar system, such as 112A and 112B, tissue remodeling energy may preferably pass through healthy tissue 303, diseased tissue 302, or a combination thereof such that remodeling zones may be created. Any number of electrodes 112 may be used in different patterns or arrays to create any number of remodeling zones. Power generator and control apparatus 101 may apply constant power, constant voltage, constant current, or modulate to produce a constant temperature, whichever has the most advantage for the type of tissue and the desired therapeutic response.

Balloon 200 is illustrated in more detail in FIG. 2. Balloon 200 generally includes a proximal portion 202 coupled to inflation lumen 201 and a distal portion 205 coupled to guidewire lumen 206. Balloon 200 expands radially when inflated with a fluid or a gas. In some embodiments, balloon 200 may be a low-pressure balloon pressurized to contact the tissue 300. In other embodiments, balloon 200 may an angioplasty balloon capable of higher pressure to both heat the tissue 300 and expand the tissue 300 lumen. Balloon 200 may comprise a compliant or non-compliant balloon having folds to facilitate reconfiguring the balloon from a radially expanded, inflated configuration to a low profile configuration, particularly for removal after use.

Electrodes 112 are mounted on a surface of balloon 200, with associated conductors 203 extending proximally from the electrodes 112. Electrodes 112 may be arranged in many different patterns or arrays on balloon 200. The system may be used for monopolar or bipolar application of energy. For delivery of monopolar energy, a ground electrode may be used either on the catheter 108 shaft or on the patient's skin, such as a ground electrode pad. For delivery of bipolar energy, adjacent electrodes 112 may be axially offset to allow bipolar energy to be directed between adjacent circumferential (axially offset) electrodes 112. In other embodiments, electrodes 112 may be arranged in bands around balloon 200 to allow bipolar energy to be directed between adjacent distal and proximal electrodes 112.

Tissue Sensing and Selective Delivery of Therapeutic Energy Dosage

In many embodiments electrodes 112 may be energized to assess and then selectively treat targeted tissue 300, 302, 303 to preferably achieve a therapeutic result. For example, tissue signature may be used to identify tissue treatment regions with the use of impedance measurements. Impedance measurements utilizing circumferentially spaced electrodes 112 within a lumen, such as those shown in FIG. 3B, may be used to analyze tissue 300, 302, 303. Impedance measurements between pairs of adjacent electrodes 112 (and/or between pairs of separated electrodes 112A-112D) may differ when the current path passes through diseased tissue 302, and when it passes through healthy tissues 303 of a luminal wall for example. Hence, impedance measurements between the electrodes 112 on either side of diseased tissue 302 may indicate a lesion, while measurements between other pairs of adjacent electrodes 112 may indicate healthy tissue 303. Other characterization, such as intravascular ultrasound, optical coherence tomography, or the like may be used to identify regions to be treated either in conjunction with, or as an alternate to, impedance measurements. In some instances, it may be desirable to obtain baseline measurements of the tissues 300, 302, 303 to be treated preferably to help differentiate adjacent tissues, as the tissue signatures and/or signature profiles may differ from person to person. Additionally, the tissue signatures and/or signature profile curves may be normalized to facilitate identification of the relevant slopes, offsets, and the like between different tissues. Any of the techniques disclosed in U.S. Patent Application No. 60/852,787, filed on Oct. 18, 2006, entitled "Tuned RF Energy and Electrical Tissue Characterization For Selective Treatment Of Target Tissues", U.S. Provisional Application No. 60/921,973, filed on Apr. 4, 2007, entitled "Tuned RF Energy and Electrical Tissue Characterization For Selective Treatment Of Target Tissues", the full disclosures of which are incorporated herein by reference, may be combined with the present invention.

The power generator and control apparatus 101 may be employed to selectively energize the electrodes 112 in a range of power from about 0.001 Watts to about 50 Watts, a preferred exemplary range of about 0.25 to 5 Watts average power for about 1 to about 180 seconds, or with about 4 to about 45 Joules. Higher energy treatments are done at lower powers and longer durations, such as about 0.5 Watts for about 90 seconds or about 0.25 Watts for about 180 seconds. Most treatments in the 2 to 4 Watt range are performed in about 1 to about 4 seconds. If using a wider electrode 112 spacing, it would be preferable to scale up the average power and duration of the treatment, in which case the average power could be higher than about 5 Watts, and the total energy could exceed about 45 Joules. Likewise, if using a shorter or smaller electrode pair 112A-112D, it would be preferable to scale the average power down, and the total energy could be less than about 4 Joules. The power and duration are calibrated to be less than enough to cause severe damage, and most preferably, particularly less than enough to ablate diseased tissue within a blood vessel.

Suitable power ranges for providing the desired heating of the target tissue, and/or for limiting of heating to collateral tissues, may depend at least in part on the time for which energy is applied, on the electrode 112 (or other energy transmitting surface) geometry, and the like. First, when applying the treatments described herein to tissues with electrodes, there may be a preferred load impedance range for the tissues within the circuit so as to avoid having to apply voltages and/or currents that are outside desirable ranges, particularly when applying powers within ranges described herein. Suitable load impedance ranges would generally be within a range from about 20 Ohms to about 4500 Ohms, more typically being in a range from about 40 Ohms to about 2250 Ohms, and preferably being in a range from about 50 to about 1000 Ohms.

The load impedance of the tissue within the circuit may depend on the characteristics of the tissue, and also for example on the geometry of electrodes that engage the tissue, as the electrode geometries and polarity influence the geometry of the tissue effectively included within the circuit. The tissue to which energy is directed may have a specific conductivity in a range from about 0.2 Siemens per meter to about 0.5 Siemens per meter. Different types of diseased tissues may have specific conductivities in different ranges, with some types of diseased tissues having specific conductivities in a range from about 0.2 Siemens per meter to about 0.35 Siemens per meter, while others fall within a range from about 0.35 Siemens per to about 0.5 Siemens per meter.

Desired power, energy, and time of the treatment are likewise inter-related, and may also be at least related with electrode 112 geometry. Speaking very generally, lower power treatments applied for long times tends to result in treatments with relatively higher total energies, while higher power treatments for shorter times tends to result in lower energy treatments. More specifically, at relatively low average power (1 W or less) the total energy delivery per treatment may range from about 8 to about 45 Joules. At higher power (more than 1 W), the total energy delivery per treatment may range from about 4 to about 15 Joules. If the electrode spacing were doubled, power may increase by four times. The power transmitted into the tissue can be calibrated and scaled to the particular electrode configuration, often in order to keep the power and energy density in a desirable range. Exemplary power ranges may be, for example, from about 1 to about 5 Watts. The duration for the lower power settings typically varies from about 1 to about 8 seconds. Very low power settings of less than about 1 Watt are also possible, using durations much longer than about 10 seconds.

It is also possible to scale the power settings significantly by varying the electrode 112 configuration. If, for instance, the inner edge-to-edge spacing of the electrodes 112 is increased, roughly 4 times the power may be applied because the volume of tissue becomes roughly 4 times larger. As such, electrode configurations different from the exemplary embodiments described herein could be used within a power range of about 4 to about 20 Watts. Shortening the electrodes 112, and thus shortening and reducing the volume of the remodeling zones, would also affect the magnitude of the power that is appropriate to apply to the tissue volume.

In order to quantify this complex set of relationships, and bound the space within which the exemplary apparatus can operate, an empirical relationship between safe values of several of these parameters may be generated and provided graphically, in table form, or by a mathematical relationships. An exemplary equation describing a particularly advantageous relationship is:

$$\text{power} = b \, x^2 L t^{-0.59}$$

where b is a parameter in the range of 0.2 to 0.6, x is the inner edge-to-edge spacing of the electrodes 112 in millimeters, L is the length of the electrodes 112 in millimeters (and also the approximate length of the remodeling zone), the power is in Watts, and t is time in seconds. b has units of $(\text{Watts/mm}^3)*(\text{seconds}^{0.59})$. Exemplary treatments in the range described by this equation include treatments such as 4 Watts for 2 seconds, 3 Watts for 3 seconds, 2 Watts for 4 seconds, and 1 Watt for 12 seconds.

Calibration of circuit 400 may be performed by taking three measurements at known circuit loads 404, most preferably, impedance $Z_{\rho O}$ is taken at load of about $1000\Omega$, impedance $Z_{\rho S}$ is taken at a load of about $50\Omega$, and impedance $Z_{\rho L}$ is taken at a load of about $150\Omega$, where the complex voltage and current measurements ($800_{V\&I}$ of FIG. 8) at power generator and control apparatus 101 are used to calculate impedances $Z_{\rho O}$, $Z_{\rho S}$, and $Z_{\rho L}$. The preferred method of calibration may allow for accurate real-time measurement of impedance before and during treatment of tissue such that impedance may provide a means for tissue characterization and treatment control as disclosed and described herein.

Calibration of apparatus 100 may further comprise the step of identifying an accessory attached to the apparatus by repeating calibration to ascertain the type of attached accessory based on its impedance characteristics. For example, in FIG. 1 where the attached accessory comprises catheter 108 further comprised of electrodes 112, the number of electrodes 112 present may be determined by multiplexed sensing of the number of electrode circuits (such as electrodes 112 and conductors 203 as shown in FIG. 2) within the catheter 108 operably attached by connector 103 to power generator and control apparatus 102. Referring once again to FIGS. 1, 4, 8, and 16, after calibration of power generator circuit 400 without accessory 100' (typically catheter 108), the catheter can be attached to the power generator circuit 1603 and three impedance measurements can again be taken of the overall apparatus 100.

A number of advantages may be gained by preferably automatically reperforming calibration. For example, by having an entire apparatus assembly 100 calibrated, rather than a single subcomponent such as the various elements of circuit 400, the impedance measurements taken at load 404 may remain an accurate indicator for tissue characterization and power control irrespective of the attached accessory. Further, the sensed configuration of an attached accessory may correspond to a programmed treatment routine such that the dependencies of assorted configurations of electrodes 112 may correspond to the preferred duration and energy delivery parameters disclosed and described herein. Even further, preprogrammed recognition of attached accessories prevents the improper use of an accessory or the use of an incompatible attachment. Even further, the ability to detect the type of attached accessory may allow for a robust and simple accessory identification method that avoids complications associated with other identification methods such as radio frequency identification that may degrade during sterilization or interfere with the operation of other equipment. Moreover, a self-identification method may reduce or eliminate the need for user commands thereby improving ease of use and minimizing issues such as language barriers between user and apparatus. Additionally, the use of a graphical user interface 102 may be used as a further means to eliminate or reduce language dependencies and increase ease of use.

In many embodiments the power generation and control apparatus 101 may be programmed to operate within a range of impedance values measured at the power delivery target 404 such that above or below set limits the system may automatically shut down. For example, the apparatus 101 may be programmed to operate over a range of load impedance from about 5 Ohms to about 1000 Ohms, having a most preferred range of about 50 Ohms to about 500 Ohms, wherein the low end of the range may be suggestive of tissue that may be healthy or responsive to tissue, and the high end of the range may be suggestive of poor electrical contact or destruction of tissue. The programmed impedance limits may provide the advantage of a further safeguard in avoiding uncontrolled application of energy to locations in excess of desired dosage.

Figure 13:
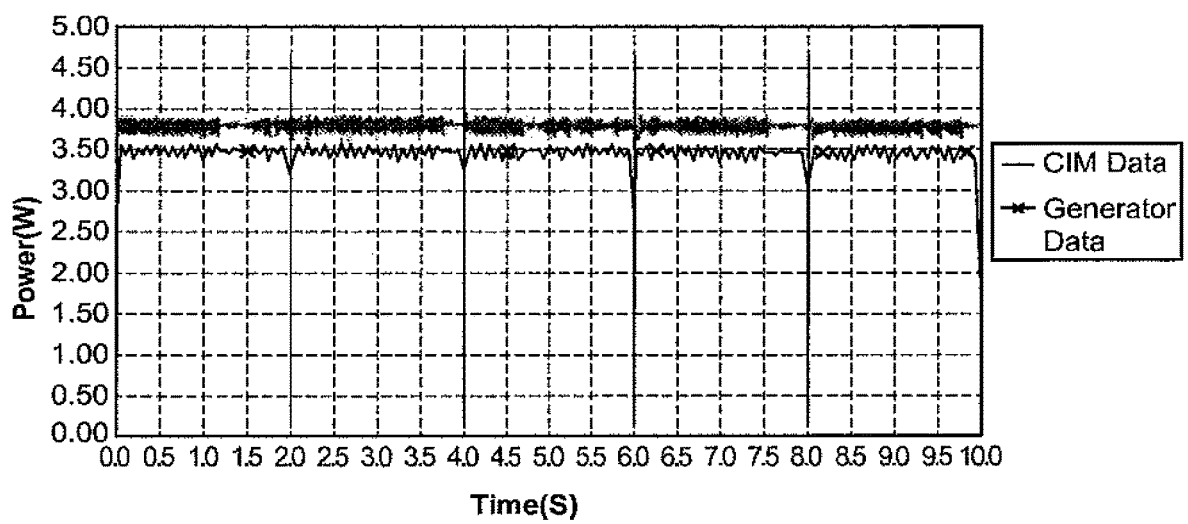
FIG. 13 is an exemplary plot of measured power at the target site and at the power generator in a tissue treatment embodiment of the apparatus shown in FIG. 1.

FIGS. 10-13 respectively show current, impedance, voltage, phase angle, and electrode power response in a typical tissue treatment employing gentle heating as controlled and delivered by the apparatus assembly of FIG. 1. In FIG. 13, the measured power at the target is shown in comparison to the power output at the generator.

Embodiments of the vascular treatment devices, systems, and methods described herein may be used to treat atherosclerotic disease by gentle heating in combination with gentle or standard dilation. For example, an angioplasty balloon catheter structure 108 having electrodes 112 disposed thereon might apply electrical potentials to the vessel wall before, during, and/or after dilation, optionally in combination with dilation pressures which are at or significantly lower than standard, unheated angioplasty dilation pressures. Where balloon 200 inflation pressures of about 10 to about 16 atmospheres may, for example, be appropriate for standard angioplasty dilation of a particular lesion, modified dilation treatments combined with appropriate electrical potentials, through flexible circuit electrodes 112, 203 on balloon 200, electrodes 112 deposited directly on the balloon structure 200, or the like, described herein may employ from about 10 to about 16 atmospheres or may be effected with pressures of about 6 atmospheres or less, and possibly as low as about 1 to about 2 atmospheres. Such moderate dilations pressures may, or may not, be combined with one or more aspects of the tissue characterization, tuned energy, eccentric treatments, and other treatment aspects described herein for treatment of diseases of the vasculature.

In many embodiments, gentle heating energy added before, during, and/or after dilation of a blood vessel may increase dilation effectiveness while lowering complications. In some embodiments, such controlled heating with balloon 200 may exhibit a reduction in recoil, providing at least some of the benefits of a stent-like expansion without the disadvantages of an implant. Benefits of the heating may be enhanced, and/or complications inhibited, by limiting heating of the vessel adventitial layer below a deleterious response threshold. In many cases, such heating of the vessel intima and/or media may be provided using heating times of less than about 10 seconds, often being less than about 3 (or even 2) seconds. In other cases, very low power may be used for longer durations. Efficient coupling of the energy 301 to the target tissue 300, 302, 303 by matching the driving potential of the circuit to the target tissue phase angle may enhance desirable heating efficiency, effectively maximizing the area under the electrical power curve. The matching of the phase angle need not be absolute, and while complete phase matching to a characterized target tissue may have benefits, alternative systems may pre-set appropriate potentials to substantially match typical target tissues; though the actual phase angles may not be matched precisely, heating localization within the target tissues may be significantly better than using a standard power form.

Remodeling may involve the application of energy, most preferably in the form of RF, but also microwave and/or ultrasound energy to electrodes 112, and the like. This energy will be controlled so as to limit a temperature of target and/or collateral tissues, for example, limiting the heating of a fibrous cap of a vulnerable plaque or the intimal layer of an artery structure.

In some embodiments, the surface tissue temperature range is from about 50° C. to about 90° C. For gentle heating, the tissue surface temperature may range from about 50° C. to about 65° C., while for more aggressive heating, the surface tissue temperature may range from about 65° C. to about 90° C. Limiting heating of a lipid-rich pool of a vulnerable plaque sufficiently to induce melting of the lipid pool while inhibiting heating of other tissues, such as an intimal layer or fibrous cap, to less than a tissue surface temperature in a range from about 50° C. to about 65° C., such that the bulk tissue temperature remains mostly below about 50° C. to about 55° C. may inhibit an immune response that might otherwise lead to restenosis, or the like. Relatively mild surface temperatures between about 50° C. and about 65° C. may be sufficient to denature and break protein bonds during treatment, immediately after treatment, and/or more than one hour, more than one day, more than one week, or even more than one month after the treatment through a healing response of the tissue to the treatment so as to provide a bigger vessel lumen and improved blood flow.

While the methods and devices described herein are not selective in tissue treatment of the blood vessels, the apparatus 100 can be used for treatment of both concentric and eccentric atherosclerosis, because atherosclerosis may be eccentric relative to an axis of the blood vessel over 50% of the time, and possibly in as much as (or even more than) 75% of cases.

Hence, remodeling of atherosclerotic materials may comprise shrinkage, melting, and the like, of atherosclerotic and other plaques. Atherosclerotic material within the layers of an artery may be denatured, melted and/or the treatment may involve a shrinking of atherosclerotic materials and/or delivery of bioactives within the artery layers so as to improve blood flow. The invention may also provide particular advantages for treatment of vulnerable plaques or blood vessels in which vulnerable plaque is a concern, which may comprise eccentric lesions. The invention will also find applications for mild heating of the cap structure to induce thickening of the cap and make the plaque less vulnerable to rupture, and/or heating of the lipid-rich pool of the vulnerable plaque so as to remodel, denature, melt, shrink, and/or redistribute the lipid-rich pool.

Controlled Application of Energy to Achieve Substantially Uniform Bulk Temperature Now referring to FIGS. 14A-15B, the controlled delivery of energy as a dosage may preferably be used to obtain a substantially uniform temperature distribution in bulk tissue by the selective distributed delivery of energy. Most preferably, tissue may be heated within a range of about 50° C. to about 70° C. to achieve a temperature preferably high enough to denature proteins and promote a healing response while avoiding tissue damage that may be caused at higher temperatures. Regulation of tissue temperature may be accomplished through direct temperature measurement using means such as a thermocouple, thermister, and the like. However, it may be advantageous to simplify the apparatus and to preferably avoid potential increases in device profile caused by the inclusion of wires or other sensing hardware into an intraluminal device. Because the present invention possesses the capability to deliver precise energy dosage and the capability to measure real-time changes in impedance at the point of power delivery, a uniform temperature distribution may be also achieved through these means.

In one preferred embodiment, tissue impedance may be used to infer tissue temperature conditions. The change in impedance as a function of time, or the derivative of the impedance slope (dz/dt), may be used to sense change in tissue temperature. Specifically, increase in impedance suggests tissue cooling given that tissue conductance is reduced as tissue cools. Conversely, decrease in impedance suggests tissue heating given that tissue conductance increases as tissue heats. Therefore, substantially constant tissue impedance, or dz/dt about equal to zero, may be used as a means to obtain a generally uniform temperature distribution through the sensing of impedance at the point of power delivery.

A distributed delivery of energy may be preferably employed to further aid in obtaining uniformity in bulk temperature. For example, electrodes 112A-L may be distributed about the circumference of a balloon. Electrodes 112A-L may be powered in a bipolar mode wherein alternate electrode pairs are powered such that in a first sequential application of energy every other electrode pair is powered at a discrete energy level for a discrete period of time. In a second sequential application of energy the electrode pairs not fired in the first sequential application of energy are powered. The configuration and ordering of power to electrode pairs to accomplish a particular temperature, for example 50° C., or 60° C., or 70° C., may be determined empirically. The duration of energy delivery in the form of sequential dosage to preferably maintain a substantially uniform temperature in the bulk tissue may then be controlled through tissue impedance measurement.

Figures 14A, 14B:
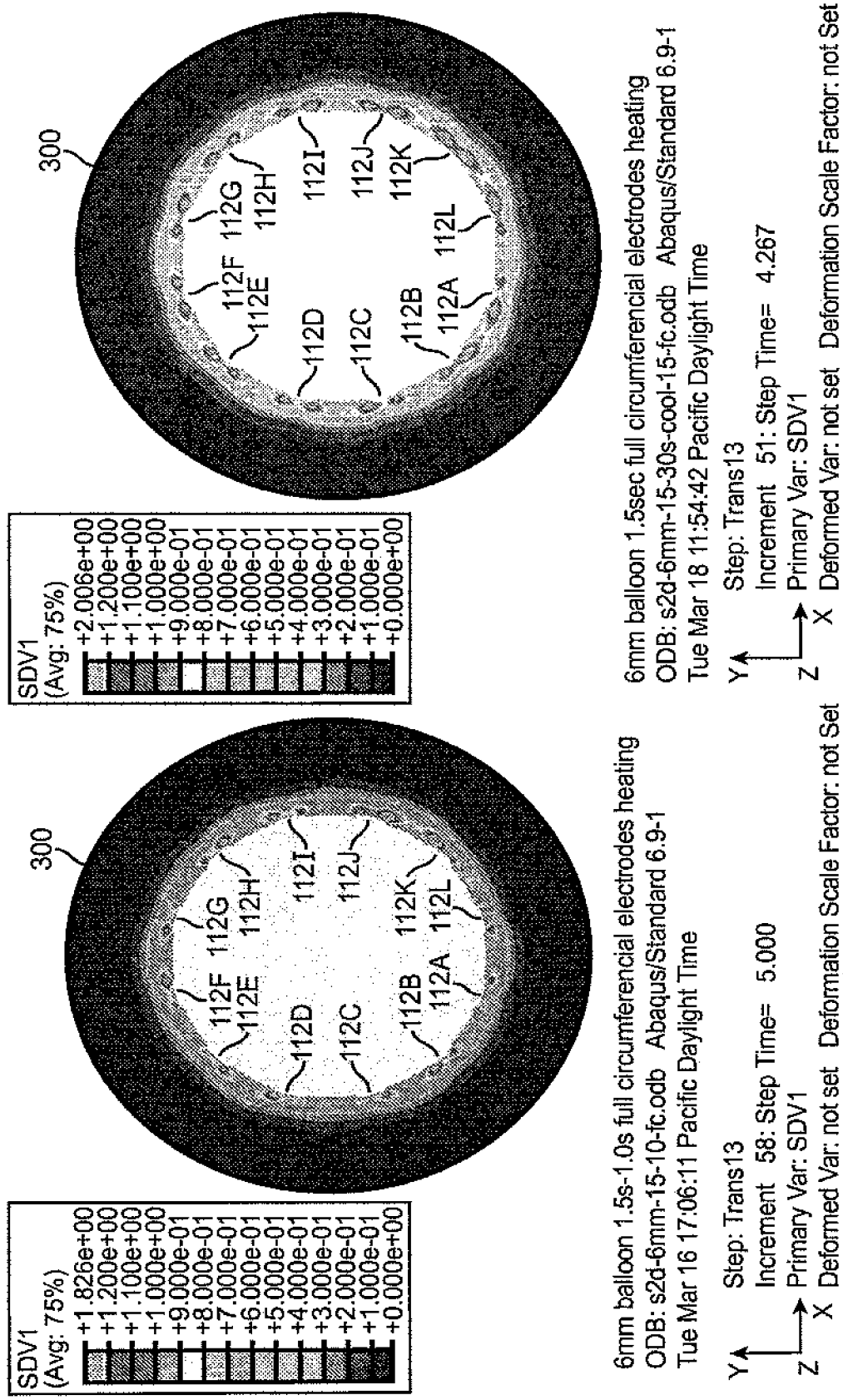
FIGS. 14A & B schematically illustrate a substantially uniform bulk temperature distribution in luminal tissue using empirically derived energy dosage and impedance control for an embodiment of the apparatus shown in FIG. 1.

Although any variety of time for power, time between power, space between electrodes powered, and total energy delivered may be employed based on the specific nature of tissue to be heated, one preferred embodiment shown in FIG. 14A shows a substantially uniform temperature distribution by sequentially powering every other electrode pair for about 1.5 seconds at about 4 Watts, followed by sequentially powering the previously unpowered electrodes for about 1 second at about 4 Watts. The benefit of spaced sequential firing is that tissue may naturally heat, hold, and begin to cool such that high concentrations of heat are preferably avoided as compared to applying power without selective distribution. Once the initial power dosage is delivered, additional power may be applied as regulated trough tissue impedance measurement. In an alternate exemplary embodiment shown in FIG. 14B, power is delivered in the same sequential manner as described for FIG. 14A, however, the second sequential application of power follows a pause of about 30 seconds and the duration of the second sequential application of power may be increased to about 1.5 seconds.

Figure 15A:
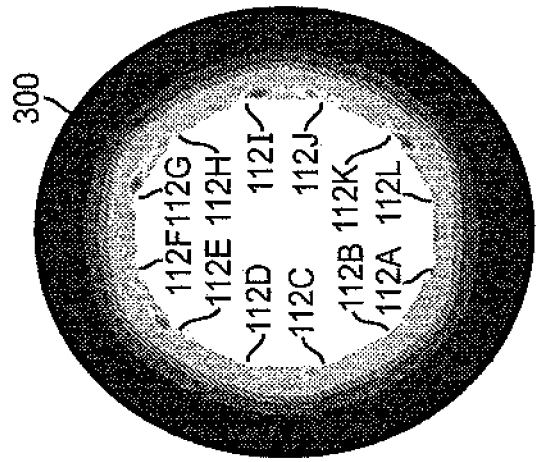
FIGS. 15A & B schematically illustrate a substantially uniform bulk temperature distribution in luminal tissue using energy dosage derived using accumulated damage theory for an embodiment of the apparatus shown in FIG. 1.
Figure 15B:
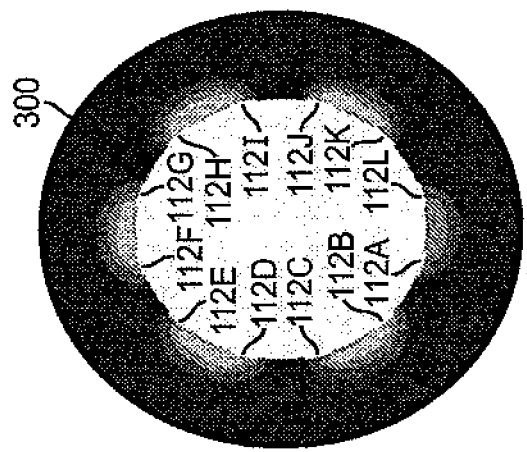

In another exemplary embodiment, shown in FIGS. 15A-B, the use of accumulated damage theory, such as that described by the Arrhenius equation, may be employed to numerically predict energy dosage such that accumulated tissue temperature effects may be used to build a power dosage routine. A first sequential power delivery between every other electrode pair at about 4 Watts for about 5 seconds may be followed by a second sequential power delivery to the previously unpowered electrode pairs wherein the power level and time duration for each electrode pair in the second sequence may vary by position such that the accumulated heating and cooling of tissue preferably is accounted for such that a substantially uniform temperature distribution may be achieved. For example, the ordered second energizing sequence of electrode pairs may be about 4 Watts for about 0.45 seconds for the first electrode pair in the sequence, about 2.6 Watts for about 0.65 seconds for the second electrode pair in the sequence, about 1.8 Watts for about 1.15 seconds at the third pair, about 1.5 Watts for about 1.65 seconds at the fourth pair, about 1.3 Watts for about 3.15 seconds at the fifth pair, and about 1.1 Watts for about 5 seconds. In this example, the accumulated effect would preferably result in a tissue temperature of about 60° C. using a balloon with 12 electrodes distributed about the outer circumference of the balloon.

The use of accumulated damage theory may be tailored to specific types of tissue based on characterized tissue response curves such that power dosage routines may be developed specifically for accomplishing a certain temperature in a certain tissue type.

Additionally, whether using a damage accumulation model, or tissue impedance measurement to maintain bulk tissue temperature at a substantially uniform distribution, the energy dosage may vary, in part, based on electrode configuration as previously described herein.

Application of Energy to Modify Nerve Activity

In yet another exemplary embodiment of the present invention, the ability to deliver energy in a targeted dosage may be used for nerve tissue in order to achieve beneficial biologic responses. For example, chronic pain, urologic dysfunction, hypertension, and a wide variety of other persistent conditions are known to be affected through the operation of nervous tissue. For example, it is known that chronic hypertension that may not be responsive to medication may be improved or eliminated by disabling excessive nerve activity proximate to the renal arteries. It is also known that nervous tissue does not naturally possess regenerative characteristics. Therefore it may be possible to beneficially affect excessive nerve activity by disrupting the conductive pathway of the nervous tissue. When disrupting nerve conductive pathways, it is particularly advantageous to avoid damage to neighboring nerves or organ tissue. The ability to direct and control energy dosage is well-suited to the treatment of nerve tissue. Whether in a heating or ablating energy dosage, the precise control of energy delivery as described and disclosed herein may be directed to the nerve tissue. Moreover, directed application of energy may suffice to target a nerve without the need be in exact contact as would be required when using a typical ablation probe. For example, eccentric heating may be applied at a temperature high enough to denature nerve tissue without causing ablation and without requiring the piercing of luminal tissue. However, it may also be preferable to configure the energy delivery surface of the present invention to pierce tissue and deliver ablating energy similar to an ablation probe with the exact energy dosage being controlled by the power control and generation apparatus 101.

Referring again to the example of renal hypertension involving the reduction of excessive nerve activity, FIG. 3B may be used to describe a non-piercing, non-ablating way to direct energy to affect nerve activity. Nerve tissue may be located in some location in tissue 300, 302, 303 surrounding the lumen of the renal artery. Electrodes 112 on balloon 200 may be powered to deliver energy 301 in the known direction of a nerve to be affected, the depth of energy penetration being a function of energy dosage. Moreover, empirical analysis may be used to determine the impedance characteristics of nervous tissue such that apparatus 101 may be used to first characterize and then treat tissue in a targeted manner as disclosed and described herein. The delivery and regulation of energy may further involve accumulated damage modeling as well.

While the exemplary embodiments have been described in some detail, by way of example and for clarity of understanding, those of skill in the art will recognize that a variety of modification, adaptations, and changes may be employed.

What is claimed is:

1. A method for the delivery of energy in tissue comprising the steps of:
    positioning a plurality of energy delivery surfaces proximate to the tissue;
    applying a first energy dosage to the tissue by powering a first portion of the plurality of energy delivery surfaces in a sequenced pattern;
    applying a second energy dosage to the tissue by powering a second portion of the plurality of energy delivery surfaces in a sequenced pattern; and
    measuring tissue impedance at a point of power delivery and applying the first and second energy dosages such that measured tissue impedance is maintained about constant, thereby resulting in a uniform temperature distribution in the tissue through the sensing of impedance at the point of power delivery;
    wherein the first and second portions of the plurality of energy delivery surfaces are powered by a power amplifier that has a soft current limit such that available output voltage decreases as output current is increased.

2. The method of claim 1, wherein the plurality of energy delivery surfaces are operatively coupled to a power generation and control apparatus further comprising: a DDS operatively coupled to the power amplifier; a power output set point controller providing a signal; a power sensor receiving voltage and current feedback measured at a power delivery target and providing a signal based on the feedback; and a PID controller, operatively coupled to receive the signals from the power output set point controller and the power sensor, and operatively coupled to direct a modulating voltage signal to the power amplifier, such that power output is maintained within a range about the power output set point in response to measured impedance at the power delivery target.

3. The method of claim 2, wherein the DDS, power output set point controller, and peak effective power sensor comprise a field programmable gate array.

4. The method of claim 2, wherein the signal from the power sensor represents the effective power output at the power delivery target.

5. The method of claim 2, wherein an available range of the power output set point is between about 0.001 Watts to about 50 Watts.

6. The method of claim 1, wherein the first and second energy dosage delivered to the tissue is RF energy.

7. The method of claim 1, wherein the energy delivery surfaces include electrodes carried on a distal end of an elongate catheter.

8. The method of claim 1, comprising positioning the plurality of energy delivery surfaces proximate to a targeted tissue region containing nerves therein.

9. The method of claim 8, further comprising characterizing the location of nerves in the tissue region by measuring the impedance of tissue proximate to the plurality of energy delivery surfaces.

10. The method of claim 8, wherein the first and second energy dosages disrupt conduction of nerve signals in the tissue region by denaturing the conductive properties of nerves in the tissue region.

11. The method of claim 8, wherein the first and second energy dosages permanently disrupt conduction of nerve signals in the tissue region by ablating nerves in the tissue region.

12. The method of claim 8, wherein power output is limited to occur at a measured impedance of tissue in the tissue region between about 50 Ohms to about 500 Ohms.

13. A method for the delivery of energy in tissue comprising the steps of:
    positioning a plurality of energy delivery surfaces proximate to the tissue;
    applying a first energy dosage to the tissue by powering a first portion of the plurality of energy delivery surfaces in a sequenced pattern;
    applying a second energy dosage to the tissue by powering a second portion of the plurality of energy delivery surfaces in a sequenced pattern; and
    measuring tissue impedance;
    wherein the plurality of energy delivery surfaces are operatively coupled to a power generation and control apparatus further comprising: a DDS operatively coupled to a power amplifier; a power output set point controller providing a signal; a power sensor receiving voltage and current feedback measured at a power delivery target and providing a signal based on the feedback; and a PID controller, operatively coupled to receive the signals from the power output set point controller and the power sensor, and operatively coupled to direct a modulating voltage signal to the power amplifier, such that power output is maintained within a range about the power output set point in response to the measured impedance at the power delivery target; and
    wherein the power amplifier is comprised of a variable gain amplifier and a linear power amplifier operatively coupled in series.

14. The method of claim 13, wherein output voltage during use comprises RF output voltage having a maximum available output limit over a range of load impedances of about 50 Ohms to about 500 Ohms.

15. A method for the delivery of energy in tissue comprising the steps of:
    positioning a plurality of energy delivery surfaces proximate to the tissue at targeted tissue region containing nerves therein;
    applying a first energy dosage to the tissue by powering a first portion of the plurality of energy delivery surfaces in a sequenced pattern;
    applying a second energy dosage to the tissue by powering a second portion of the plurality of energy delivery surfaces in a sequenced pattern; and
    measuring tissue impedance at a point of power delivery and applying the first and second energy dosages such that measured tissue impedance is maintained about constant, thereby resulting in a uniform temperature distribution in the tissue through the sensing of impedance at the point of power delivery;
    wherein the energy delivery surfaces include electrodes carried on a distal end of an elongate catheter;
    wherein the first and second energy dosage delivered to the tissue is RF energy; and
    wherein the first and second portions of the plurality of energy delivery surfaces are powered by a power amplifier that has a soft current limit such that available output voltage decreases as output current is increased.

16. The method of claim 15, further comprising characterizing the location of nerves in the tissue region by measuring the impedance of tissue proximate to the plurality of energy delivery surfaces.

17. The method of claim 15, wherein the first and second energy dosages disrupt conduction of nerve signals in the tissue region by denaturing the conductive properties of nerves in the tissue region.

18. The method of claim 15, wherein the first and second energy dosages permanently disrupt conduction of nerve signals in the tissue region by ablating nerves in the tissue region.

19. The method of claim 15, wherein power output is limited to occur at a measured impedance of tissue in the tissue region between about 50 Ohms to about 500 Ohms.

20. The method of claim 15, wherein the plurality of energy delivery surfaces are operatively coupled to a power generation and control apparatus further comprising: a DDS operatively coupled to the power amplifier; a power output set point controller providing a signal; a power sensor receiving voltage and current feedback measured at a power delivery target and providing a signal based on the feedback; and a PID controller, operatively coupled to receive the signals from the power output set point controller and the power sensor, and operatively coupled to direct a modulating voltage signal to the power amplifier, such that power output is maintained within a range about the power output set point in response to measured impedance at the power delivery target.

\* \* \* \* \*